(12) United States Patent
Jung et al.

(10) Patent No.: US 11,650,209 B2
(45) Date of Patent: May 16, 2023

(54) FC-GAMMA RECEPTOR MUTANTS

(71) Applicant: KOOKMIN UNIVERSITY INDUSTRY ACADEMY COOPERATION FOUNDATION, Seoul (KR)

(72) Inventors: Sang Taek Jung, Gyeonggi-do (KR); Migyeong Jo, Gyeonggi-do (KR); Sanghwan Ko, Seoul (KR); Bora Hwang, Gyeonggi-do (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 322 days.

(21) Appl. No.: 16/628,427

(22) PCT Filed: Sep. 13, 2018

(86) PCT No.: PCT/KR2018/010783
§ 371 (c)(1),
(2) Date: Jan. 3, 2020

(87) PCT Pub. No.: WO2019/054782
PCT Pub. Date: Mar. 21, 2019

(65) Prior Publication Data
US 2020/0408778 A1 Dec. 31, 2020

(30) Foreign Application Priority Data

| Sep. 15, 2017 | (KR) | 10-2017-0118769 |
| Sep. 15, 2017 | (KR) | 10-2017-0118770 |
| Sep. 15, 2017 | (KR) | 10-2017-0118771 |
| Oct. 12, 2017 | (KR) | 10-2017-0132862 |
| Oct. 12, 2017 | (KR) | 10-2017-0132863 |
| Oct. 12, 2017 | (KR) | 10-2017-0132864 |

(51) Int. Cl.
| *G01N 33/53* | (2006.01) |
| *C12N 5/00* | (2006.01) |
| *C12N 15/00* | (2006.01) |
| *C07K 16/46* | (2006.01) |
| *G01N 33/68* | (2006.01) |
| *C07K 14/735* | (2006.01) |
| *A61K 38/00* | (2006.01) |

(52) U.S. Cl.
CPC ............. *G01N 33/6857* (2013.01); *C07K 14/70535* (2013.01); *A61K 38/00* (2013.01); *C07K 16/46* (2013.01); *C07K 2319/31* (2013.01); *C12N 5/00* (2013.01); *C12N 15/00* (2013.01); *G01N 33/53* (2013.01)

(58) Field of Classification Search
None
See application file for complete search history.

(56) References Cited

U.S. PATENT DOCUMENTS

| 5,985,599 | A | 11/1999 | McKenzie et al. |
| 2002/0107359 | A1* | 8/2002 | Hogarth ............... A61P 37/02 |
| | | | 702/19 |
| 2007/0207163 | A1 | 9/2007 | Sondermann et al. |
| 2010/0196372 | A1 | 8/2010 | Johnson et al. |
| 2012/0021484 | A1 | 1/2012 | McDonnell |
| 2014/0107034 | A1* | 4/2014 | Birks ..................... A61P 7/00 |
| | | | 435/320.1 |
| 2016/0200807 | A1* | 7/2016 | Ruike ................. G01N 33/6872 |
| | | | 424/139.1 |

FOREIGN PATENT DOCUMENTS

WO WO-2017054033 A1 * 4/2017 ....... C07K 14/70535

OTHER PUBLICATIONS

Morel. Mouse models of human autoimmune diseases: Essential tools that require proper controls, Plos Biology vol. 2/No. 8:1061-1064 (Aug. 2004). (Year: 2004).*
Doehn et al. Pentraxin-3 levels in graft-versus-host disease during allogeneic hematopoietic stem cell transplantation. Experimental Hematology vol. 44:917-923; (2016). (Year: 2016).*
Justice et al. Using the mouse to model human disease: increasing validity and reproducibility, Disease, Models & Mechanisms 9: 101-103, (2016). (Year: 2016).*
Phillips, A., The challenge of gene therapy and DNA delivery. J Pharm Pharmacology 53: 1169-1174, (2001). (Year: 2001).*
West et al. Gene Therapy for Pulmonary Diseases. Chest 2001; 119:613-617; (2001). (Year: 2001).*
Ierino eot al., "Recombinant Soluble Human FcyRII: Production, Characterization, and Inhibition of the Arthus Reaction", Journal of Experimental Medicine, Nov. 1993, vol. 178, pp. 1617-1628.
Sondermann et al. "Harnessing Fc receptor biology in design of therapeutic antibodies", Current Opinion in Immunology, 2016, vol. 40, pp. 78-87.
Kontermann, R.E., et al.,"Half-life extended biotherapeutics," Expert Opinion on Biological Therapy, 2016, 16:7, pp. 903-915.
Schlapschy, M., et al., "PASylation: a biological alternative to PEGylation for extending the plasma half-life of pharmaceutically active proteins," Protein Engineering, Design & Selection, 2013, vol. 26, No. 8, pp. 489-501.
Podust, V.N., et al., "Extension of in vivo half-life of biologically active molecules by XTEN protein polymers," Journal of Controlled Release, 2016, 240, 52-66.

(Continued)

*Primary Examiner* — Elizabeth C. Kemmerer
*Assistant Examiner* — Regina M DeBerry
(74) *Attorney, Agent, or Firm* — Duane Morris LLP; Gregory M. Lefkowitz; Brandon A. Chan

(57) ABSTRACT

The present disclosure relates to a polypeptide including an Fc-gamma receptor mutant. The Fc-gamma receptor mutant of the present disclosure is optimized by substituting a part of an amino acid sequence of an Fc-gamma receptor with a different amino acid sequence, so as to provide an excellent selective binding ability to immunoglobulins. Therefore, it can be usefully used for increasing in vivo half-life of drugs, detecting and purifying immunoglobulins, inhibiting organ transplant rejections, or preventing or treating autoimmune diseases.

13 Claims, 19 Drawing Sheets

Specification includes a Sequence Listing.

(56) References Cited

OTHER PUBLICATIONS

Roopenian, D.C., et al., "FcRn: the neonatal Fc receptor comes of age," Nature Reviews, Immunology, Sep. 2007, vol. 7, pp. 715-725.

Nimmerjahn, F., et al., "Fcy receptors as regulators of immune responses," Nature Reviews, Immunology, Jan. 2008, vol. 8, pp. 34-47.

Park, H.I., et al., "The Highly Evolvable Antibody Fc Domain," Trends in Biotechnology, Nov. 2016, vol. 34, No. 11, pp. 895-908.

Asaoka, Y., et al., "Engineering of recombinant human Fcy receptor I by directed evolution," Protein Engineering, Design & Selection, 2012, vol. 25, No. 12, pp. 835-842.

Jo, M., et al., "Engineered human FcyRIIa fusion: A novel strategy to extend serum half-life of therapeutic proteins," Biotechnology and Bioengineering, Jan. 2020, 117, 2351-2361.

Zaman, R., et al., "Current strategies in extending half-lives of therapeutic proteins," Journal of Controlled Release, 2019, 301, 176-189.

\* cited by examiner

SEQUENCE LISTING

```
<160> NUMBER OF SEQ ID NOS: 63

<210> SEQ ID NO 1
<211> LENGTH: 48
<212> TYPE: DNA
<213> ORGANISM: Artificial Sequence
<220> FEATURE:
<223> OTHER INFORMATION: primer-P788
<220> FEATURE:
<221> NAME/KEY: variation
<222> LOCATION: (21)..(22)
<223> OTHER INFORMATION: n is a, g, c or t.
<220> FEATURE:
<221> NAME/KEY: variation
<222> LOCATION: (24)..(25)
<223> OTHER INFORMATION: n is a, g, c or t.
<220> FEATURE:
<221> NAME/KEY: variation
<222> LOCATION: (27)..(28)
<223> OTHER INFORMATION: n is a, g, c or t.

<400> SEQUENCE: 1
gcggggtttg cagcaccagm nnmnnmnnaa gcacggtcag atgcaccg                 48

<210> SEQ ID NO 2
<211> LENGTH: 48
<212> TYPE: DNA
<213> ORGANISM: Artificial Sequence
<220> FEATURE:
<223> OTHER INFORMATION: primer-P789
<220> FEATURE:
<221> NAME/KEY: variation
<222> LOCATION: (21)..(22)
<223> OTHER INFORMATION: n is a, g, c or t.
<220> FEATURE:
<221> NAME/KEY: variation
<222> LOCATION: (24)..(25)
<223> OTHER INFORMATION: n is a, g, c or t.
<220> FEATURE:
<221> NAME/KEY: variation
<222> LOCATION: (27)..(28)
<223> OTHER INFORMATION: n is a, g, c or t.

<400> SEQUENCE: 2
cggtgcatct gaccgtgctt nnknnknnkc tggtgctgca aaccccgc                 48

<210> SEQ ID NO 3
<211> LENGTH: 66
<212> TYPE: DNA
<213> ORGANISM: Artificial Sequence
<220> FEATURE:
<223> OTHER INFORMATION: primer-P790
<220> FEATURE:
<221> NAME/KEY: variation
<222> LOCATION: (32)..(33)
<223> OTHER INFORMATION: n is a, g, c or t.
<220> FEATURE:
<221> NAME/KEY: variation
<222> LOCATION: (38)..(39)
<223> OTHER INFORMATION: n is a, g, c or t.
<220> FEATURE:
```

<221> NAME/KEY: variation
<222> LOCATION: (41)..(42)
<223> OTHER INFORMATION: n is a, g, c or t.

<400> SEQUENCE: 3
gcttttgcca ttctgaaaaa aggtcacttt mnncagmnnm nnatctttcc agctatggca    60
acgcag    66

<210> SEQ ID NO 4
<211> LENGTH: 66
<212> TYPE: DNA
<213> ORGANISM: Artificial Sequence
<220> FEATURE:
<223> OTHER INFORMATION: primer-P791
<220> FEATURE:
<221> NAME/KEY: variation
<222> LOCATION: (25)..(26)
<223> OTHER INFORMATION: n is a, g, c or t.
<220> FEATURE:
<221> NAME/KEY: variation
<222> LOCATION: (28)..(29)
<223> OTHER INFORMATION: n is a, g, c or t.
<220> FEATURE:
<221> NAME/KEY: variation
<222> LOCATION: (34)..(35)
<223> OTHER INFORMATION: n is a, g, c or t.

<400> SEQUENCE: 4
ctgcgttgcc atagctggaa agatnnknnk ctgnnkaaag tgaccttttt tcagaatggc    60
aaaagc    66

<210> SEQ ID NO 5
<211> LENGTH: 74
<212> TYPE: DNA
<213> ORGANISM: Artificial Sequence
<220> FEATURE:
<223> OTHER INFORMATION: primer-P792
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (33)..(34)
<223> OTHER INFORMATION: n is a, g, c or t.
<220> FEATURE:
<221> NAME/KEY: variation
<222> LOCATION: (42)..(43)
<223> OTHER INFORMATION: n is a, g, c or t.

<400> SEQUENCE: 5
gcggaatgct aaaggtcgga tccagmnnag amnntttctg mnntttgcca ttctgaaaaa    60
aggtcacttt cacc    74

<210> SEQ ID NO 6
<211> LENGTH: 74
<212> TYPE: DNA
<213> ORGANISM: Artificial Sequence
<220> FEATURE:
<223> OTHER INFORMATION: primer-P793
<220> FEATURE:
<221> NAME/KEY: variation
<222> LOCATION: (32)..(33)
<223> OTHER INFORMATION: n is a, g, c or t.
<220> FEATURE:
<221> NAME/KEY: variation
<222> LOCATION: (41)..(42)
<223> OTHER INFORMATION: n is a, g, c or t.
<220> FEATURE:
<221> NAME/KEY: variation
<222> LOCATION: (47)..(48)
<223> OTHER INFORMATION: n is a, g, c or t.

<400> SEQUENCE: 6
ggtgaaagtg acctttttc agaatggcaa annkcagaaa nnktctnnkc tggatccgac    60
ctttagcatt ccgc    74

<210> SEQ ID NO 7
<211> LENGTH: 34
<212> TYPE: DNA
<213> ORGANISM: Artificial Sequence
<220> FEATURE:
<223> OTHER INFORMATION: IIa_Fw_NdeI

<400> SEQUENCE: 7
gcggaattcc atatgcaggc tgccccaccg aaag    34

<210> SEQ ID NO 8
<211> LENGTH: 32
<212> TYPE: DNA
<213> ORGANISM: Artificial Sequence
<220> FEATURE:
<223> OTHER INFORMATION: IIa_Rv_HindIII

<400> SEQUENCE: 8
taagggaagc ttaatcacgc ccatcggtga gc    32

<210> SEQ ID NO 9
<211> LENGTH: 20
<212> TYPE: DNA
<213> ORGANISM: Artificial Sequence
<220> FEATURE:
<223> OTHER INFORMATION: primer-MJ#1

<400> SEQUENCE: 9
ccaggcttta cactttatgc    20

<210> SEQ ID NO 10
<211> LENGTH: 19
<212> TYPE: DNA
<213> ORGANISM: Artificial Sequence
<220> FEATURE:
<223> OTHER INFORMATION: primer-MJ#2

<400> SEQUENCE: 10
ctgcccatgt tgacgattg    19

<210> SEQ ID NO 11
<211> LENGTH: 26
<212> TYPE: DNA
<213> ORGANISM: Artificial Sequence
<220> FEATURE:
<223> OTHER INFORMATION: primer-MJ#112

<400> SEQUENCE: 11
cagcggttta tctttccagc tatggc    26

<210> SEQ ID NO 12
<211> LENGTH: 72
<212> TYPE: DNA
<213> ORGANISM: Artificial Sequence
<220> FEATURE:
<223> OTHER INFORMATION: primer-MJ#113
<220> FEATURE:
<221> NAME/KEY: variation
<222> LOCATION: (27)..(28)

```
<223> OTHER INFORMATION: n is a, g, c or t.
<220> FEATURE:
<221> NAME/KEY: variation
<222> LOCATION: (30)..(31)
<223> OTHER INFORMATION: n is a, g, c or t.
<220> FEATURE:
<221> NAME/KEY: variation
<222> LOCATION: (36)..(37)
<223> OTHER INFORMATION: n is a, g, c or t.

<400> SEQUENCE: 12
gccatagctg gaaagataaa ccgctgnnkn nggtgnnktt ttttcagaat ggcaaaagcc      60
agaaattttc tc                                                         72

<210> SEQ ID NO 13
<211> LENGTH: 72
<212> TYPE: DNA
<213> ORGANISM: Artificial Sequence
<220> FEATURE:
<223> OTHER INFORMATION: primer-MJ#114
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (36)..(37)
<223> OTHER INFORMATION: n is a, g, c or t.

<400> SEQUENCE: 13
gccatagctg gaaagataaa ccgctgnnkg atgtgnnktt ttttcagaat ggcaaaagcc      60
agaaattttc tc                                                         72

<210> SEQ ID NO 14
<211> LENGTH: 72
<212> TYPE: DNA
<213> ORGANISM: Artificial Sequence
<220> FEATURE:
<223> OTHER INFORMATION: primer-MJ#115
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (36)..(37)
<223> OTHER INFORMATION: n is a, g, c or t.

<400> SEQUENCE: 14
gccatagctg gaaagataaa ccgctgnnkt ttgtgnnktt ttttcagaat ggcaaaagcc      60
agaaattttc tc                                                         72

<210> SEQ ID NO 15
<211> LENGTH: 72
<212> TYPE: DNA
<213> ORGANISM: Artificial Sequence
<220> FEATURE:
<223> OTHER INFORMATION: primer-MJ#116
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (36)..(37)
<223> OTHER INFORMATION: n is a, g, c or t.
```

<400> SEQUENCE: 15
gccatagctg gaaagataaa ccgctgnnkc atgtgnnktt ttttcagaat ggcaaaagcc       60
agaaattttc tc       72

<210> SEQ ID NO 16
<211> LENGTH: 72
<212> TYPE: DNA
<213> ORGANISM: Artificial Sequence
<220> FEATURE:
<223> OTHER INFORMATION: primer-MJ#117
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (36)..(37)
<223> OTHER INFORMATION: n is a, g, c or t.

<400> SEQUENCE: 16
gccatagctg gaaagataaa ccgctgnnka ttgtgnnktt ttttcagaat ggcaaaagcc       60
agaaattttc tc       72

<210> SEQ ID NO 17
<211> LENGTH: 72
<212> TYPE: DNA
<213> ORGANISM: Artificial Sequence
<220> FEATURE:
<223> OTHER INFORMATION: primer-MJ#118
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (36)..(37)
<223> OTHER INFORMATION: n is a, g, c or t.

<400> SEQUENCE: 17
gccatagctg gaaagataaa ccgctgnnkt atgtgnnktt ttttcagaat ggcaaaagcc       60
agaaattttc tc       72

<210> SEQ ID NO 18
<211> LENGTH: 72
<212> TYPE: DNA
<213> ORGANISM: Artificial Sequence
<220> FEATURE:
<223> OTHER INFORMATION: primer-MJ#119
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (30)..(31)
<223> OTHER INFORMATION: n is a, g, c or t.
<220> FEATURE:
<221> NAME/KEY: variation
<222> LOCATION: (36)
<223> OTHER INFORMATION: n is a, g, c or t.

<400> SEQUENCE: 18
gccatagctg gaaagataaa ccgctgnnkn nggtgnwktt ttttcagaat ggcaaaagcc       60
agaaattttc tc       72

<210> SEQ ID NO 19
<211> LENGTH: 72
<212> TYPE: DNA
<213> ORGANISM: Artificial Sequence
<220> FEATURE:
<223> OTHER INFORMATION: primer-MJ#120
<220> FEATURE:
<221> NAME/KEY: variation
<222> LOCATION: (27)..(28)
<223> OTHER INFORMATION: n is a, g, c or t
<220> FEATURE:
<221> NAME/KEY: variation
<222> LOCATION: (30)..(31)
<223> OTHER INFORMATION: n is a, g, c or t

<400> SEQUENCE: 19
gccatagctg gaaagataaa ccgctgnnkn nkgtggcgtt ttttcagaat ggcaaaagcc    60
agaaattttc tc    72

<210> SEQ ID NO 20
<211> LENGTH: 72
<212> TYPE: DNA
<213> ORGANISM: Artificial Sequence
<220> FEATURE:
<223> OTHER INFORMATION: primer-MJ#121
<220> FEATURE:
<221> NAME/KEY: variation
<222> LOCATION: (27)..(28)
<223> OTHER INFORMATION: n is a, g, c or t
<220> FEATURE:
<221> NAME/KEY: variation
<222> LOCATION: (30)..(31)
<223> OTHER INFORMATION: n is a, g, c or t

<400> SEQUENCE: 20
gccatagctg gaaagataaa ccgctgnnkn nkgtgggctt ttttcagaat ggcaaaagcc    60
agaaattttc tc    72

<210> SEQ ID NO 21
<211> LENGTH: 72
<212> TYPE: DNA
<213> ORGANISM: Artificial Sequence
<220> FEATURE:
<223> OTHER INFORMATION: primer-MJ#122
<220> FEATURE:
<221> NAME/KEY: variation
<222> LOCATION: (27)..(28)
<223> OTHER INFORMATION: n is a, g, c or t
<220> FEATURE:
<221> NAME/KEY: variation
<222> LOCATION: (30)..(31)
<223> OTHER INFORMATION: n is a, g, c or t

<400> SEQUENCE: 21
gccatagctg gaaagataaa ccgctgnnkn nkgtgccgtt ttttcagaat ggcaaaagcc    60
agaaattttc tc    72

<210> SEQ ID NO 22
<211> LENGTH: 72
<212> TYPE: DNA
<213> ORGANISM: Artificial Sequence
<220> FEATURE:
<223> OTHER INFORMATION: primer-MJ#123
<220> FEATURE:
<221> NAME/KEY: variation
<222> LOCATION: (27)..(28)
<223> OTHER INFORMATION: n is a, g, c or t
<220> FEATURE:

```
<221> NAME/KEY: variation
<222> LOCATION: (30)..(31)
<223> OTHER INFORMATION: n is a, g, c or t.

<400> SEQUENCE: 22
gccatagctg gaaagataaa ccgctgnnkn nkgtgcgttt ttttcagaat ggcaaaagcc    60
agaaattttc tc                                                       72

<210> SEQ ID NO 23
<211> LENGTH: 72
<212> TYPE: DNA
<213> ORGANISM: Artificial Sequence
<220> FEATURE:
<223> OTHER INFORMATION: primer-MJ#124
<220> FEATURE:
<221> NAME/KEY: variation
<222> LOCATION: (27)..(28)
<223> OTHER INFORMATION: n is a, g, c or t.
<220> FEATURE:
<221> NAME/KEY: variation
<222> LOCATION: (30)..(31)
<223> OTHER INFORMATION: n is a, g, c or t.

<400> SEQUENCE: 23
gccatagctg gaaagataaa ccgctgnnkn nkgtgtggtt ttttcagaat ggcaaaagcc    60
agaaattttc tc                                                       72

<210> SEQ ID NO 24
<211> LENGTH: 26
<212> TYPE: DNA
<213> ORGANISM: Artificial Sequence
<220> FEATURE:
<223> OTHER INFORMATION: primer-MJ#160

<400> SEQUENCE: 24
cgcagcgaga ggcccagccg gccatg                                        26

<210> SEQ ID NO 25
<211> LENGTH: 23
<212> TYPE: DNA
<213> ORGANISM: Artificial Sequence
<220> FEATURE:
<223> OTHER INFORMATION: primer-MJ#161

<400> SEQUENCE: 25
cgcaattcgg ccccgaggc ccc                                            23

<210> SEQ ID NO 26
<211> LENGTH: 36
<212> TYPE: DNA
<213> ORGANISM: Artificial Sequence
<220> FEATURE:
<223> OTHER INFORMATION: primer-MJ#162

<400> SEQUENCE: 26
cgcagcgagc gcgcactcca tgcaggctgc cccacc                             36

<210> SEQ ID NO 27
<211> LENGTH: 34
<212> TYPE: DNA
<213> ORGANISM: Artificial Sequence
<220> FEATURE:
<223> OTHER INFORMATION: primer-MJ#163

<400> SEQUENCE: 27
ccctaaaatc tagaaatcac gcccatcggt gagc                               34
```

<210> SEQ ID NO 28
<211> LENGTH: 35
<212> TYPE: DNA
<213> ORGANISM: Artificial Sequence
<220> FEATURE:
<223> OTHER INFORMATION: primer-MJ#197

<400> SEQUENCE: 28
cgggaaaatt tcttggattt tccattctgg aagaa    35

<210> SEQ ID NO 29
<211> LENGTH: 67
<212> TYPE: DNA
<213> ORGANISM: Artificial Sequence
<220> FEATURE:
<223> OTHER INFORMATION: primer-MJ#198

<400> SEQUENCE: 29
gctggaagga caagcctctg gtcaatgtcg tgttcttcca gaatggaaaa tccaagaaat    60
tttcccg    67

<210> SEQ ID NO 30
<211> LENGTH: 54
<212> TYPE: DNA
<213> ORGANISM: Artificial Sequence
<220> FEATURE:
<223> OTHER INFORMATION: primer-MJ#199

<400> SEQUENCE: 30
cgcaattcgg cccccgaggc cccgggctct tggacagtga tggtcacagg cttg    54

<210> SEQ ID NO 31
<211> LENGTH: 27
<212> TYPE: DNA
<213> ORGANISM: Artificial Sequence
<220> FEATURE:
<223> OTHER INFORMATION: primer-MJ#200

<400> SEQUENCE: 31
cagcccagct accatttcaa ggccaac    27

<210> SEQ ID NO 32
<211> LENGTH: 27
<212> TYPE: DNA
<213> ORGANISM: Artificial Sequence
<220> FEATURE:
<223> OTHER INFORMATION: primer-MJ#201

<400> SEQUENCE: 32
gttggccttg aaatggtagc tgggctg    27

<210> SEQ ID NO 33
<211> LENGTH: 29
<212> TYPE: DNA
<213> ORGANISM: Artificial Sequence
<220> FEATURE:
<223> OTHER INFORMATION: primer-MJ#202

<400> SEQUENCE: 33
cataggctac acgcagtact catccaagc    29

<210> SEQ ID NO 34
<211> LENGTH: 29
<212> TYPE: DNA

```
<213> ORGANISM: Artificial Sequence
<220> FEATURE:
<223> OTHER INFORMATION: primer-MJ#203

<400> SEQUENCE: 34
gcttggatga gtactgcgtg tagcctatg                                    29

<210> SEQ ID NO 35
<211> LENGTH: 549
<212> TYPE: DNA
<213> ORGANISM: Homo sapiens

<400> SEQUENCE: 35
gccccaccga aagccgtgct gaaactggaa ccgccgtgga ttaatgtgtt gcaggaagat   60
agcgtgaccc tgacctgtca gggagcgcgt agccctgaaa gcgattctat tcagtggttt  120
cacaatggaa atctgattcc gacccatacc cagccgagct atcgttttaa agcgaacaat  180
aatgatagcg gcgaatacac ctgccagacg ggccagacca gcctgagcga tccggtgcat  240
ctgaccgtgc ttagcgaatg gctggtgctg caaaccccgc atctggaatt tcaggaaggc  300
gaaaccatta tgctgcgttg ccatagctgg aaagataaac cgctggtgaa agtgaccttt  360
tttcagaatg gcaaaagcca gaatttttct cacctggatc cgacctttag cattccgcag  420
gcgaatcatt ctcactccgg cgattaccat tgtaccggca atataggcta taccctgttt  480
agcagcaaac cggtgacaat taccgtgcag gtgccgagca tgggcagcag ctcaccgatg  540
ggcgtgatt                                                          549

<210> SEQ ID NO 36
<211> LENGTH: 549
<212> TYPE: DNA
<213> ORGANISM: Artificial Sequence
<220> FEATURE:
<223> OTHER INFORMATION: SH2A40

<400> SEQUENCE: 36
gccccaccga aagccgtgct gaaactggaa ccgccgtgga ttaatgtgtt gcaggaagat   60
agcgtgaccc tgacctgtca gggagcgcgt agccctgaaa gcgattctat tcagtggttt  120
cacaatggaa atctgattcc gacccatacc cagccgagct atcgttttaa agcgaacaat  180
aatgatagcg gcgaatacac ctgccagacg ggccagacca gcctgagcga tccggtgcat  240
ctgaccgtgc ttagcgaatg gctggtgctg caaaccccgc atctggaatt tcaggaaggc  300
gaaaccatta tgctgcgttg ccatagctgg aaagataaac cgctggtgaa tgtgaccttt  360
tttcagaacg gcaaaagcca gaatttttct cacctggatc cgacctttag cattccgcag  420
gcgaatcatt ctcactccgg cgattaccat tgtaccggca atataggcta tacccagttt  480
agcagcaaac cggtgacaat taccgtgcag gtgccgagca tgggcagcag ctcaccgatg  540
ggcgtgatt                                                          549

<210> SEQ ID NO 37
<211> LENGTH: 549
<212> TYPE: DNA
<213> ORGANISM: Artificial Sequence
<220> FEATURE:
<223> OTHER INFORMATION: MG2A28

<400> SEQUENCE: 37
gccccaccga aagccgtgct gaaactggaa ccgccgtgga ttaatgtgtt gcaggaagat   60
agcgtgaccc tgacctgtca gggagcgcgt agccctgaaa gcgattctat tcagtggttt  120
```

```
cacaatggaa atctgattcc gacccatacc cagccgagct atcgttttaa agcgaacaat    180
aatgatagcg gcgaatacac ctgccagacg ggccagacca gcctgagcga tccggtgcat    240
ctgaccgtgc ttagcgaatg gctggtgctg caaaccccgc atctggaatt tcaggaaggc    300
gaaaccatta tgctgcgttg ccatagctgg aaagataaac cgctggtgaa tgtgatgttt    360
tttcagaatg gcaaaagcca gaaatttttct cacctggatc cgacctttag cattccgcag    420
gcgaatcatt ctcactccgg cgattaccat tgtaccggca atataggcta tcccagtttt    480
agcagcaaac cggtgacaat taccgtgcag gtgccgagca tgggcagcag ctcaccgatg    540
ggcgtgatt                                                            549

<210> SEQ ID NO 38
<211> LENGTH: 549
<212> TYPE: DNA
<213> ORGANISM: Artificial Sequence
<220> FEATURE:
<223> OTHER INFORMATION: MG2A45

<400> SEQUENCE: 38
gccccaccga aagccgtgct gaaactggaa ccgccgtgga ttaatgtgtt gcaggaagat     60
agcgtgaccc tgacctgtca gggagcgcgt agccctgaaa gcgattctat tcagtggttt    120
cacaatggaa atctgattcc gacccatacc cagccgagct atcgttttaa agcgaacaat    180
aatgatagcg gcgaatacac ctgccagacg ggccagacca gcctgagcga tccggtgcat    240
ctgaccgtgc ttagcgaatg gctggtgctg caaaccccgc atctggaatt tcaggaaggc    300
gaaaccatta tgctgcgttg ccatagctgg aaagataaac cgctggtgaa tgtggtgttt    360
tttcagaatg gcaaaagcca gaaatttttct cacctggatc cgacctttag cattccgcag    420
gcgaatcatt ctcactccgg cgattaccat tgtaccggca atataggcta tcccagtttt    480
agcagcaaac cggtgacaat taccgtgcag gtgccgagca tgggcagcag ctcaccgatg    540
ggcgtgatt                                                            549

<210> SEQ ID NO 39
<211> LENGTH: 549
<212> TYPE: DNA
<213> ORGANISM: Artificial Sequence
<220> FEATURE:
<223> OTHER INFORMATION: MG2A28.1

<400> SEQUENCE: 39
gccccaccga aagccgtgct gaaactggaa ccgccgtgga ttaatgtgtt gcaggaagat     60
agcgtgaccc tgacctgtca gggagcgcgt agccctgaaa gcgattctat tcagtggttt    120
cacaatggaa atctgattcc gacccatacc cagccgagct atcgttttaa agcgaacaat    180
aatgatagcg gcgaatacac ctgccagacg ggccagacca gcctgagcga tccggtgcat    240
ctgaccgtgc ttagcgattg gctggtgctg caaaccccgc atctggaatt tcaggaaggc    300
gaaaccatta tgctgcgttg ccatagctgg aaagataaac cgctggtgaa tgtgatgttt    360
tttcagaatg gcaaaagcct gaaatttttct cacctggatc cgacctttag cattccgcag    420
gcgaatcatt ctcactccgg cgattaccat tgtaccggca atataggcta tcccagtttt    480
agcagcaaac cggtgacaat taccgtgcag gagccgagca tgggcagcag ctcaccgatg    540
ggcgtgatt                                                            549

<210> SEQ ID NO 40
```

```
<211> LENGTH: 549
<212> TYPE: DNA
<213> ORGANISM: Artificial Sequence
<220> FEATURE:
<223> OTHER INFORMATION: MG2A45.1

<400> SEQUENCE: 40
gccccaccga aagccgtgct gaaactggaa ccgccgtgga ttaatgtgtt gcaggaagat      60
agcgtgaccc tgacctgtca gggagcgcgt agccctgaaa gcgattctat tcagtggttt    120
cacaatggaa atctgattcc gacccatacc cagccgagct atcattttaa agcgaacaat    180
aatgatagcg gcgaatacac ctgccagacg ggccagacca gcctgagcga tccggtgcat    240
ctgaccgtgc ttagcgaatg gctggtgctg caaaccccgc atctggaatt tcaggaaggc    300
gaaaccatta tgctgcgttg ccatagctgg aaagataaac cgctggtgaa tgtggtgttt    360
tttcagaatg gcaaaagcca gaaatttttct cacctggatc cgacctttag cattccgcag   420
gcgaatcatt ctcactccgg cgattaccat tgtaccggca atataggcta tcccagttt     480
agcagcaaac cggtgacaat taccgtgcag gagccgagca tgggcagcag ctcaccgatg    540
ggcgtgatt                                                            549

<210> SEQ ID NO 41
<211> LENGTH: 516
<212> TYPE: DNA
<213> ORGANISM: Homo sapiens

<400> SEQUENCE: 41
gctcccccaa aggctgtgct gaaactcgag ccccagtgga tcaacgtgct ccaggaggac     60
tctgtgactc tgacatgccg ggggactcac agccctgaga gcgactccat tcagtggttc    120
cacaatggga atctcattcc cacccacacg cagcccagct acaggttcaa ggccaacaac    180
aatgacagcg gggagtacac gtgccagact ggccagacca gcctcagcga ccctgtgcat    240
ctgactgtgc tttccgaatg gctggtgctc cagacccctc acctggagtt ccaggaggga    300
gaaaccatcg tgctgaggtg ccacagctgg aaggacaagc ctctggtcaa ggtcacattc    360
ttccagaatg gaaaatccaa gaaattttcc cgttcggatc ccaacttctc catcccacaa    420
gcaaaccaca gtcacagtgg tgattaccac tgcacaggaa acataggcta cacgctgtac    480
tcatccaagc tgtgaccat cactgtccaa gctccc                                516

<210> SEQ ID NO 42
<211> LENGTH: 516
<212> TYPE: DNA
<213> ORGANISM: Artificial Sequence
<220> FEATURE:
<223> OTHER INFORMATION: MG2B45.1

<400> SEQUENCE: 42
gctcccccaa aggctgtgct gaaactcgag ccccagtgga tcaacgtgct ccaggaggac     60
tctgtgactc tgacatgccg ggggactcac agccctgaga gcgactccat tcagtggttc    120
cacaatggga atctcattcc cacccatacc cagccgagct atcattttaa agcgaacaat    180
aatgatagcg gcgaatacac gtgccagact ggccagacca gcctcagcga ccctgtgcat    240
ctgactgtgc tttccgaatg gctggtgctc cagacccctc acctggagtt ccaggaggga    300
gaaaccatcg tgctgaggtg ccacagctgg aaggacaagc ctctggtcaa tgtcgtgttc    360
ttccagaatg gaaaatccaa gaaattttcc cgttcggatc ccaacttctc catcccacaa    420
gcaaaccaca gtcacagtgg tgattaccac tgcacaggaa acataggcta cacgcagtac    480
```
tcatccaagc ctgtgaccat cactgtccaa gagccc                    516

<210> SEQ ID NO 43
<211> LENGTH: 183
<212> TYPE: PRT
<213> ORGANISM: Homo sapiens

<400> SEQUENCE: 43

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Lys Val Thr Phe Phe Gln Asn Gly Lys Ser Gln Lys
        115                 120                 125

Phe Ser His Leu Asp Pro Thr Phe Ser Ile Pro Gln Ala Asn His Ser
    130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Val Pro Ser Met Gly Ser
                165                 170                 175

Ser Ser Pro Met Gly Val Ile
            180

<210> SEQ ID NO 44
<211> LENGTH: 183
<212> TYPE: PRT
<213> ORGANISM: Artificial Sequence
<220> FEATURE:
<223> OTHER INFORMATION: SH2A40

<400> SEQUENCE: 44

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

```
Lys Pro Leu Val Asn Val Thr Phe Phe Gln Asn Gly Lys Ser Gln Lys
            115                 120                 125

Phe Ser His Leu Asp Pro Thr Phe Ser Ile Pro Gln Ala Asn His Ser
        130                 135                 140

His Ser Gly Asp Tyr His Cys Thr Gly Asn Ile Gly Tyr Thr Gln Phe
145                 150                 155                 160

Ser Ser Lys Pro Val Thr Ile Thr Val Gln Val Pro Ser Met Gly Ser
            165                 170                 175

Ser Ser Pro Met Gly Val Ile
            180

<210> SEQ ID NO 45
<211> LENGTH: 183
<212> TYPE: PRT
<213> ORGANISM: Artificial Sequence
<220> FEATURE:
<223> OTHER INFORMATION: MG2A28

<400> SEQUENCE: 45

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Asn Val Met Phe Phe Gln Asn Gly Lys Ser Gln Lys
            115                 120                 125

Phe Ser His Leu Asp Pro Thr Phe Ser Ile Pro Gln Ala Asn His Ser
        130                 135                 140

His Ser Gly Asp Tyr His Cys Thr Gly Asn Ile Gly Tyr Thr Gln Phe
145                 150                 155                 160

Ser Ser Lys Pro Val Thr Ile Thr Val Gln Val Pro Ser Met Gly Ser
            165                 170                 175

Ser Ser Pro Met Gly Val Ile
            180

<210> SEQ ID NO 46
<211> LENGTH: 183
<212> TYPE: PRT
<213> ORGANISM: Artificial Sequence
<220> FEATURE:
<223> OTHER INFORMATION: MG2A45

<400> SEQUENCE: 46

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30
```

Glu Ser Asp Ser Ile Gln Trp Phe His Asn Gly Asn Leu Ile Pro Thr
            35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Asn Val Phe Phe Gln Asn Gly Lys Ser Gln Lys
        115                 120                 125

Phe Ser His Leu Asp Pro Thr Phe Ser Ile Pro Gln Ala Asn His Ser
130                 135                 140

His Ser Gly Asp Tyr His Cys Thr Gly Asn Ile Gly Tyr Thr Gln Phe
145                 150                 155                 160

Ser Ser Lys Pro Val Thr Ile Thr Val Gln Val Pro Ser Met Gly Ser
                165                 170                 175

Ser Ser Pro Met Gly Val Ile
            180

<210> SEQ ID NO 47
<211> LENGTH: 183
<212> TYPE: PRT
<213> ORGANISM: Artificial Sequence
<220> FEATURE:
<223> OTHER INFORMATION: MG2A28.1

<400> SEQUENCE: 47

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
            35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
65                  70                  75                  80

Leu Thr Val Leu Ser Asp Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Asn Val Met Phe Phe Gln Asn Gly Lys Ser Leu Lys
        115                 120                 125

Phe Ser His Leu Asp Pro Thr Phe Ser Ile Pro Gln Ala Asn His Ser
130                 135                 140

His Ser Gly Asp Tyr His Cys Thr Gly Asn Ile Gly Tyr Thr Gln Phe
145                 150                 155                 160

Ser Ser Lys Pro Val Thr Ile Thr Val Gln Glu Pro Ser Met Gly Ser
                165                 170                 175

Ser Ser Pro Met Gly Val Ile
            180

<210> SEQ ID NO 48

```
<211> LENGTH: 183
<212> TYPE: PRT
<213> ORGANISM: Artificial Sequence
<220> FEATURE:
<223> OTHER INFORMATION: MG2A45.1

<400> SEQUENCE: 48
```

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr His Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Asn Val Val Phe Gln Asn Gly Lys Ser Gln Lys
        115                 120                 125

Phe Ser His Leu Asp Pro Thr Phe Ser Ile Pro Gln Ala Asn His Ser
    130                 135                 140

His Ser Gly Asp Tyr His Cys Thr Gly Asn Ile Gly Tyr Thr Gln Phe
145                 150                 155                 160

Ser Ser Lys Pro Val Thr Ile Thr Val Gln Glu Pro Ser Met Gly Ser
                165                 170                 175

Ser Ser Pro Met Gly Val Ile
            180

```
<210> SEQ ID NO 49
<211> LENGTH: 172
<212> TYPE: PRT
<213> ORGANISM: Homo sapiens

<400> SEQUENCE: 49
```

Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
    130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro
                165                 170

<210> SEQ ID NO 50
<211> LENGTH: 172
<212> TYPE: PRT
<213> ORGANISM: Artificial Sequence
<220> FEATURE:
<223> OTHER INFORMATION: MG2B45.1

<400> SEQUENCE: 50

Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
            20                  25                  30

Glu Ser Asp Ser Ile Gln Trp Phe His Asn Gly Asn Leu Ile Pro Thr
        35                  40                  45

His Thr Gln Pro Ser Tyr His Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Asn Val Val Phe Phe Gln Asn Gly Lys Ser Lys Lys
        115                 120                 125

Phe Ser Arg Ser Asp Pro Asn Phe Ser Ile Pro Gln Ala Asn His Ser
    130                 135                 140

His Ser Gly Asp Tyr His Cys Thr Gly Asn Ile Gly Tyr Thr Gln Tyr
145                 150                 155                 160

Ser Ser Lys Pro Val Thr Ile Thr Val Gln Glu Pro
                165                 170

<210> SEQ ID NO 51
<211> LENGTH: 40
<212> TYPE: DNA
<213> ORGANISM: Artificial Sequence
<220> FEATURE:
<223> OTHER INFORMATION: BR#1

<400> SEQUENCE: 51
cgcagcgagc gcgcactccg aggtgcagct ggtggagagc                            40

<210> SEQ ID NO 52
<211> LENGTH: 26
<212> TYPE: DNA
<213> ORGANISM: Artificial Sequence
<220> FEATURE:
<223> OTHER INFORMATION: BR#2

<400> SEQUENCE: 52
actagagaca gtcaccagtg taccct                                           26

<210> SEQ ID NO 53
<211> LENGTH: 113
<212> TYPE: DNA
<213> ORGANISM: Artificial Sequence
<220> FEATURE:

<223> OTHER INFORMATION: BR#3

<400> SEQUENCE: 53

```
agggtacact ggtgactgtc tctagtggtg gaggcggatc aggcggtggc ggcagtggag      60
ggggtggtag cggcggagga ggttccgaca tccagatgac tcaatcaccc agt            113
```

<210> SEQ ID NO 54
<211> LENGTH: 73
<212> TYPE: DNA
<213> ORGANISM: Artificial Sequence
<220> FEATURE:
<223> OTHER INFORMATION: BR#4

<400> SEQUENCE: 54

```
ccctaaaatc tagatcacta gtgatggtga tgatgatgtg atccgccggt ccgcttaatc      60
tccactttgg ttc                                                        73
```

<210> SEQ ID NO 55
<211> LENGTH: 26
<212> TYPE: DNA
<213> ORGANISM: Artificial Sequence
<220> FEATURE:
<223> OTHER INFORMATION: BR#5

<400> SEQUENCE: 55

```
ggtccgctta atctccactt tggttc                                          26
```

<210> SEQ ID NO 56
<211> LENGTH: 60
<212> TYPE: DNA
<213> ORGANISM: Artificial Sequence
<220> FEATURE:
<223> OTHER INFORMATION: BR#6

<400> SEQUENCE: 56

```
gaaccaaagt ggagattaag cggaccggcg gaggcgggag tcaggctgcc ccaccgaaag      60
```

<210> SEQ ID NO 57
<211> LENGTH: 69
<212> TYPE: DNA
<213> ORGANISM: Artificial Sequence
<220> FEATURE:
<223> OTHER INFORMATION: BR#7

<400> SEQUENCE: 57

```
ttttagggtc tagatcacta gtgatggtga tgatgatgtg atccgccaat cacgcccatc      60
ggtgagctg                                                             69
```

<210> SEQ ID NO 58
<211> LENGTH: 756
<212> TYPE: DNA
<213> ORGANISM: Artificial Sequence
<220> FEATURE:
<223> OTHER INFORMATION: Bevacizumab scFv

<400> SEQUENCE: 58

```
gaagtccagc tggtggagtc cgtggcggc ctcgtgcagc ctgggggtc attgcgccta        60
tcatgcgcag cctccggata tactttaca aactacggaa tgaactgggt gcggcaagcc      120
cccggaaaag gcctggagtg ggtgggttgg atcaatacct ataccggtga accaacatat     180
gctgctgact caagaggag atttaccttc tccctggaca ctagtaagtc tacagcttat      240
ctgcagatga atagcctgcg agccgaggat accgcagttt attactgtgc taaatatcct     300
```

```
cactattatg gatcttctca ctggtatttt gatgtgtggg gccagggcac tcttgttaca    360
gtaagcagtg gtggaggcgg atcaggcggt ggcggcagtg gaggggtgg tagcggcgga     420 ggaggttccg acatccagat gactcaatca cccagttcac tgtctgcgtc tgttggggat   480
cgggtgacca ttacgtgctc cgcctctcaa gacattagta actatctcaa ctggtatcaa    540
cagaaaccag gcaaagcccc taaggtgttg atatacttca cctccagcct gcacagcggt    600
gttccgtcac gcttttctgg cagtggctcc gggacggact tcacactcac aatctcgagc    660
ctgcaacccg aggacttcgc aacctactat tgccagcagt actccaccgt ccctggacc     720 tttggccagg gaaccaaagt ggagattaag cggacc                              756

<210> SEQ ID NO 59
<211> LENGTH: 1326
<212> TYPE: DNA
<213> ORGANISM: Artificial Sequence
<220> FEATURE:
<223> OTHER INFORMATION: Bevacizumab scFv-Fc gamma RIIa wild type

<400> SEQUENCE: 59
gaagtccagc tggtggagtc cggtggcggc ctcgtgcagc ctgggggtc attgcgccta      60 tcatgcgcag cctccggata cttttaca aactacggaa tgaactgggt gcggcaagcc     120
cccggaaaag gcctggagtg ggtggttgg atcaatacct ataccggtga accaacatat     180
gctgctgact tcaagaggag atttaccttc tccctggaca ctagtaagtc tacagcttat    240
ctgcagatga atagcctgcg agccgaggat accgcagttt attactgtgc taaatatcct    300
cactattatg gatcttctca ctggtatttt gatgtgtggg gccagggcac tcttgttaca    360
gtaagcagtg gtggaggcgg atcaggcggt ggcggcagtg gaggggtgg tagcggcgga     420 ggaggttccg acatccagat gactcaatca cccagttcac tgtctgcgtc tgttggggat   480
cgggtgacca ttacgtgttc cgcctctcaa gacattagta actatctcaa ctggtatcaa    540
cagaaaccag gcaaagcccc taaggtgttg atatacttca cctccagcct gcacagcggt    600
gttccgtcac gcttttctgg cagtggctcc gggacggact tcacactcac aatctcgagc    660
ctgcaacccg aggacttcgc aacctactat tgccagcagt actccaccgt ccctggacc     720 tttggccagg gaaccaaagt ggagattaag cggaccggcg gaggcgggag tcaggctgcc    780
ccaccgaaag ccgtgctgaa actggaaccg ccgtggatta atgtgttgca ggaagatagc    840
gtgaccctga cctgtcaggg agcgcgtagc cctgaaagcg attctattca gtggtttcac    900
aatgaaaatc tgattccgac ccatacccag ccgagctatc gttttaaagc gaacaataat    960
gatagcggcg aatacacctg ccagacgggc cagaccagcc tgagcgatcc ggtgcatctg   1020
accgtgctta gcgaatggct ggtgctgcaa accccgcatc tggaatttca ggaaggcgaa   1080
accattatgc tgcgttgcca gctggaaa gataaaccgc tggtgaaagt gacctttttt    1140
cagaatggca aaagccagaa attttctcac ctggatccga cctttagcat tccgcaggcg   1200
aatcattctc actccggcga ttaccattgt accggcaata taggctatac cctgtttagc   1260
agcaaaccgg tgacaattac cgtgcaggtg ccgagcatgg gcagcagctc accgatgggc   1320
gtgatt                                                              1326

<210> SEQ ID NO 60
<211> LENGTH: 1326
<212> TYPE: DNA
<213> ORGANISM: Artificial Sequence
<220> FEATURE:
```

<223> OTHER INFORMATION: Bevacizumab scFv-MG2A45.1

<400> SEQUENCE: 60

```
gaagtccagc tggtggagtc cggtggcggc ctcgtgcagc tggggggtc attgcgccta      60
tcatgcgcag cctccggata tactttttaca aactacggaa tgaactgggt gcggcaagcc    120
cccggaaaag gcctggagtg ggtgggttgg atcaatacct ataccggtga accaacatat    180
gctgctgact tcaagaggag atttacctttc tccctggaca ctagtaagtc tacagcttat    240
ctgcagatga atagcctgcg agccgaggat accgcagttt attactgtgc taaatatcct    300
cactattatg gatcttctca ctggtatttt gatgtgtggg gccagggcac tcttgttaca    360
gtaagcagtg gtggaggcgg atcaggcggt ggcggcagtg gaggggtgg tagcggcgga    420
ggaggttccg acatccagat gactcaatca cccagttcac tgtctgcgtc tgttggggat    480
cgggtgacca ttacgtgctc cgcctctcaa gacattagta ctatctcaa ctggtatcaa    540
cagaaaccag gcaaagcccc taaggtgttg atatacttca cctccagcct gcacagcggt    600
gttccgtcac gcttttctgg cagtggctcc gggacggact tcacactcac aatctcgagc    660
ctgcaacccg aggacttcgc aacctactat tgccagcagt actccaccgt ccctggacc    720
tttggccagg gaaccaaagt ggagattaag cggaccggcg gaggcgggag tcaggctgcc    780
ccaccgaaag ccgtgctgaa actggaaccg ccgtggatta atgtgttgca ggaagatagc    840
gtgaccctga cctgtcaggg agcgcgtagc cctgaaagcg attctattca gtggtttcac    900
aatggaaatc tgattccgac ccatacccag ccgagctatc attttaaagc gaacaataat    960
gatagcggcg aatacacctg ccagacgggc cagaccagcc tgagcgatcc ggtgcatctg   1020
accgtgctta gcgaatggct ggtgctgcaa accccgcatc tggaatttca ggaaggcgaa   1080
accattatgc tgcgttgcca tagctggaaa gataaaccgc tggtgaatgt ggtgtttttt   1140
cagaatggca aaagccagaa attttctcac ctggatccga cctttagcat tccgcaggcg   1200
aatcattctc actccggcga ttaccattgt accggcaata taggctatac ccagtttagc   1260
agcaaaccgg tgacaattac cgtgcaggag ccgagcatgg gcagcagctc accgatgggc   1320
gtgatt                                                              1326
```

<210> SEQ ID NO 61
<211> LENGTH: 252
<212> TYPE: PRT
<213> ORGANISM: Artificial Sequence
<220> FEATURE:
<223> OTHER INFORMATION: Bevacizumab scFv

<400> SEQUENCE: 61

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Gly Gly Gly Gly Ser Asp
            130                 135                 140

Ile Gln Met Thr Gln Ser Pro Ser Ser Leu Ser Ala Ser Val Gly Asp
145                 150                 155                 160

Arg Val Thr Ile Thr Cys Ser Ala Ser Gln Asp Ile Ser Asn Tyr Leu
                165                 170                 175

Asn Trp Tyr Gln Gln Lys Pro Gly Lys Ala Pro Lys Val Leu Ile Tyr
            180                 185                 190

Phe Thr Ser Ser Leu His Ser Gly Val Pro Ser Arg Phe Ser Gly Ser
            195                 200                 205

Gly Ser Gly Thr Asp Phe Thr Leu Thr Ile Ser Ser Leu Gln Pro Glu
            210                 215                 220

Asp Phe Ala Thr Tyr Tyr Cys Gln Gln Tyr Ser Thr Val Pro Trp Thr
225                 230                 235                 240

Phe Gly Gln Gly Thr Lys Val Glu Ile Lys Arg Thr
            245                 250

<210> SEQ ID NO 62
<211> LENGTH: 442
<212> TYPE: PRT
<213> ORGANISM: Artificial Sequence
<220> FEATURE:
<223> OTHER INFORMATION: Bevacizumab scFv-Fc gamma RIIa wild type

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Gly Gly Gly Gly Ser Asp
            130                 135                 140

Ile Gln Met Thr Gln Ser Pro Ser Ser Leu Ser Ala Ser Val Gly Asp
145                 150                 155                 160

Arg Val Thr Ile Thr Cys Ser Ala Ser Gln Asp Ile Ser Asn Tyr Leu
                165                 170                 175

Asn Trp Tyr Gln Gln Lys Pro Gly Lys Ala Pro Lys Val Leu Ile Tyr
            180                 185                 190

Phe Thr Ser Ser Leu His Ser Gly Val Pro Ser Arg Phe Ser Gly Ser
            195                 200                 205

Gly Ser Gly Thr Asp Phe Thr Leu Thr Ile Ser Ser Leu Gln Pro Glu
            210                 215                 220

Asp Phe Ala Thr Tyr Tyr Cys Gln Gln Tyr Ser Thr Val Pro Trp Thr
225                 230                 235                 240

Phe Gly Gln Gly Thr Lys Val Glu Ile Lys Arg Thr Gly Gly Gly Gly
                245                 250                 255

Ser Gln Ala Ala Pro Lys Ala Val Leu Lys Leu Glu Pro Pro Trp
        260                 265                 270

Ile Asn Val Leu Gln Glu Asp Ser Val Thr Leu Thr Cys Gln Gly Ala
            275                 280                 285

Arg Ser Pro Glu Ser Asp Ser Ile Gln Trp Phe His Asn Gly Asn Leu
        290                 295                 300

Ile Pro Thr His Thr Gln Pro Ser Tyr Arg Phe Lys Ala Asn Asn Asn
305                 310                 315                 320

Asp Ser Gly Glu Tyr Thr Cys Gln Thr Gly Gln Thr Ser Leu Ser Asp
                325                 330                 335

Pro Val His Leu Thr Val Leu Ser Glu Trp Leu Val Leu Gln Thr Pro
            340                 345                 350

His Leu Glu Phe Gln Glu Gly Glu Thr Ile Met Leu Arg Cys His Ser
        355                 360                 365

Trp Lys Asp Lys Pro Leu Val Lys Val Thr Phe Phe Gln Asn Gly Lys
370                 375                 380

Ser Gln Lys Phe Ser His Leu Asp Pro Thr Phe Ser Ile Pro Gln Ala
385                 390                 395                 400

Asn His Ser His Ser Gly Asp Tyr His Cys Thr Gly Asn Ile Gly Tyr
                405                 410                 415

Thr Leu Phe Ser Ser Lys Pro Val Thr Ile Thr Val Gln Val Pro Ser
            420                 425                 430

Met Gly Ser Ser Ser Pro Met Gly Val Ile
        435                 440

<210> SEQ ID NO 63
<211> LENGTH: 442
<212> TYPE: PRT
<213> ORGANISM: Artificial Sequence
<220> FEATURE:
<223> OTHER INFORMATION: Bevacizumab scFv-MG2A45.1

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Gly Gly Gly Gly Ser
        115                 120                 125

```
Gly Gly Gly Gly Ser Gly Gly Gly Ser Gly Gly Gly Ser Asp
    130             135             140

Ile Gln Met Thr Gln Ser Pro Ser Ser Leu Ser Ala Ser Val Gly Asp
145             150              155             160

Arg Val Thr Ile Thr Cys Ser Ala Ser Gln Asp Ile Ser Asn Tyr Leu
                165             170              175

Asn Trp Tyr Gln Gln Lys Pro Gly Lys Ala Pro Lys Val Leu Ile Tyr
            180             185              190

Phe Thr Ser Ser Leu His Ser Gly Val Pro Ser Arg Phe Ser Gly Ser
        195              200             205

Gly Ser Gly Thr Asp Phe Thr Leu Thr Ile Ser Ser Leu Gln Pro Glu
    210             215             220

Asp Phe Ala Thr Tyr Tyr Cys Gln Gln Tyr Ser Thr Val Pro Trp Thr
225             230             235             240

Phe Gly Gln Gly Thr Lys Val Glu Ile Lys Arg Thr Gly Gly Gly Gly
                245             250             255

Ser Gln Ala Ala Pro Pro Lys Ala Val Leu Lys Leu Glu Pro Pro Trp
        260             265             270

Ile Asn Val Leu Gln Glu Asp Ser Val Thr Leu Thr Cys Gln Gly Ala
        275             280             285

Arg Ser Pro Glu Ser Asp Ser Ile Gln Trp Phe His Asn Gly Asn Leu
    290             295             300

Ile Pro Thr His Thr Gln Pro Ser Tyr His Phe Lys Ala Asn Asn Asn
305         310             315             320

Asp Ser Gly Glu Tyr Thr Cys Gln Thr Gly Gln Thr Ser Leu Ser Asp
                325             330             335

Pro Val His Leu Thr Val Leu Ser Glu Trp Leu Val Leu Gln Thr Pro
            340             345             350

His Leu Glu Phe Gln Glu Gly Glu Thr Ile Met Leu Arg Cys His Ser
        355             360             365

Trp Lys Asp Lys Pro Leu Val Asn Val Val Phe Phe Gln Asn Gly Lys
    370             375             380

Ser Gln Lys Phe Ser His Leu Asp Pro Thr Phe Ser Ile Pro Gln Ala
385             390             395             400

Asn His Ser His Ser Gly Asp Tyr His Cys Thr Gly Asn Ile Gly Tyr
                405             410             415

Thr Gln Phe Ser Ser Lys Pro Val Thr Ile Thr Val Gln Glu Pro Ser
            420             425             430

Met Gly Ser Ser Ser Pro Met Gly Val Ile
    435             440
```

FC-GAMMA RECEPTOR MUTANTS

CROSS-REFERENCE TO RELATED APPLICATIONS

This application is a § 371 national stage entry of International Application No. PCT/KR2018/010783, filed on September 13, 2018, which claims priority to Korean Patent Application No. 10-2017-0118769, filed Sep. 15, 2017, Korean Patent Application No. 10-2017-0118770, filed Sep. 15, 2017, Korean Patent Application No. 10-2017-0118771, filed Sep. 15, 2017, Korean Patent Application No. 10-2017-0132862, filed Oct. 12, 2017, Korean Patent Application No. 10-2017-0132863, filed Oct. 12, 2017, and Korean Patent Application No. 10-2017-0132864, filed Oct. 12, 2017, the entire contents of which are incorporated herein by reference.

TECHNICAL FIELD

The present disclosure relates to Fc-gamma receptor mutants with improved binding ability to IgG antibodies.

BACKGROUND ART

Fc-gamma receptors (FcγRI, FcγRIIa, FcγRIIb, FcγRIIIa) expressed in human immune cells bind to the Fc regions (lower hinge region and upper CH2 region) of IgG antibodies. Among these Fc-gamma receptors, FcγRI has the highest affinity for IgG in blood. But, because of very poor thermostability and low expression level, there are difficulties in medical or industrial applications.

Meanwhile, FcγRIIa is a transmembrane protein expressed on the surface of various immune cells such as macrophages, monocytes, neutrophils, etc. It is a receptor with a relatively low affinity ($K_D=\sim 10^{-6}$) for IgG. FcγRIIa binds to the Fc regions (lower hinge region and upper CH2 region) of IgG antibodies and activates the immune cells via intracellular signaling mechanisms.

If it is possible to produce and administer a soluble Fc-gamma receptor existing in the extracellular region and having remarkably higher affinity for IgG than the wild-type Fc-gamma receptor, the binding of autoantibodies recognizing autologous cells as antigens to the Fc-gamma receptor on the surface of the immune cells can be inhibited effectively. This can be definitely helpful in treating autoimmune disease, which is a condition where autoantibodies are accumulated in organs and autologous cells are recognized as foreign antigens, leading to inflammations.

In general, most protein drugs excluding antibodies have short in vivo retention time and serum half-life not exceeding 24 hours. The antibody IgG is randomly brought into a cell by pinocytosis and then released into bloodstream of neutral pH without being degraded in endosomes of weakly acidic pH by binding to FcRn. Therefore, it is retained in vivo for about 3 weeks. The process of the Fc-gamma receptor binding to the antibody IgG may be utilized for development of a fusion partner that increases the serum half-life of protein drugs.

Demands on protein drugs exhibiting high specificity for target diseases and few side effects are increasing steadily and, in line with this, researches for improving the efficacy and stability of protein drugs are being carried out actively throughout the world. In particular, because the serum half-life of a protein drug plays a critical role in the mechanism of action, degree of side effects, therapeutic efficacy, production cost, number of administrations, etc. of the protein, researches for increasing the half-life of protein drugs are being carried out actively by world's leading pharmaceutical companies and protein engineering research groups.

As representative examples, the target protein is modified with a PEG (polyethylene glycol) polymer or the target protein is fused with the antibody Fc or albumin to increase serum half-life.

If a biocompatible polymer such as PEG is conjugated at a specific site of the target protein or it is nonspecifically bound to several sites, degradation by proteases may be decreased. In addition, excretion at the kidneys may be decreased and blood retention time may be increased due to increased molecular weight. Since the PEG-modified adenosine deaminase developed in 1990 by Enzon was approved by USFDA and released in the market, more than 10 products are commercially available and used for clinical applications. Roche modified interferon-α with the PEG polymer (PEGylation) for use as a therapeutic agent for hepatitis C and commercialized it under the brand name Pegasys. Amgen modified the N-terminal of filgrastim (Neupogen), which was developed to treat leukopenia, with 20-kDa PEG for commercialization of a sustained duration form, Neulasta. However, when the protein is injected in large quantities, the PEG moiety is removed slowly from the body. In addition, it is reported that long-term injection of the high-molecular-weight PEG may cause side effects. Serum stability is closely related with the molecular weight of PEG. A PEG with a molecular weight of 40,000 Da or higher is not easy to prepare and it is known that, as the molecular weight is increased, yield is decreased due to low reactivity with the protein and the titer of the protein itself is also decreased rapidly. In addition, because the PEG polymer is a mixture of polymers having various molecular weight distributions, a protein therapeutic agent conjugated with PEG is heterogeneous and causes difficulties in production and quality control. Accordingly, development of a new protein engineering technology distinguished form modification with a polymer such as PEG is urgently needed to increase the serum half-life of protein drugs.

Various Fc-fusion protein drugs fused with the antibody Fc are being studied and developed to improve the serum half-life of protein drugs having pharmacological effects. The fusion of a therapeutic protein with the Fc region of a human antibody will make it possible to utilize cell recycling mechanism through binding to the FcRn receptor. A technology of connecting interferon-α and an Fc fragment with a peptide linker was developed in 1998, and a fusion protein obtained by connecting human erythropoietin and Fc with a peptide linker was developed in 2003. As a representative example, etanercept (Enbrel®) is an inhibitor of TNF-α, which a major cytokine causing arthritis. It is a protein drug obtained by fusing a part of the TNF-α receptor existing outside a cell with the Fc fragment of an immunoglobulin. At present, ten Fc fusion proteins including etanercept are approved by the USFDA and used for clinical applications. However, the protein therapeutic agents fused with the Fc fragment have the cytotoxicity problem due to the intrinsic immune cell-activating function of Fc and are disadvantageous in that half-life is not increased significantly due to receptor-mediated clearance. In addition, because they should be fused with the Fc fragment existing as a homodimer, there is a problem that the pharmacological activity of the target protein is changed.

A method of increasing the serum half-life of protein therapeutic agents using albumin which exists at high level in human serum, instead of the Fc fragment, as a fusion partner is also being studied. Protein drugs including human growth hormone, interferon, etc. fused with albumin are under clinical development by Human Genome Sciences holding the albumin fusion technology. Because albumin is a macroprotein with a large molecular weight (66.5 kDa), the resulting fusion protein may inhibit the activity of the target protein.

It is expected that a technology using an FcγR mutant will be applied to various protein therapeutic agents and candidate proteins to improve serum half-life greatly. In addition, many peptide drugs that have pharmacological efficacy but are limited in clinical applications due to short in vivo half-life and residence time may be fused with the FcγR mutant to increase serum half-life greatly. Accordingly, it is expected that the drug will exert efficacy at the target tissue for a long time, leading to significant reduction of administration dosage and frequency, reduced cost of new drug development, and greatly increased feasibility of new drug development.

An autoimmune disease is a condition where antibodies produced in the body recognize autologous cells and immune cells attack the autologous cells through immune response. The immune cells have FcγRs that can bind to the antibodies. Binding to the antibodies leads to immune response such as ADCC or ADCP. Accordingly, soluble FcγRIIa, which binds to the antibody recognizing autologous cells and blocks binding of recognized autologous cells to immune cells, may be advantageously developed into a therapeutic agent for autoimmune disease. For this purpose, a drug which inhibits autoimmune disease using the wild-type soluble FcγRIIb with not high IgG affinity is under phase II clinical trial (Sondermann et. al., *Curr Opin Immunol*, 2016).

The above description given in the Background section is merely for improving the understanding of the background of the present disclosure, and should not be interpreted as acknowledging that it corresponds to prior art previously known to those of ordinary skill in the art.

DISCLOSURE

Technical Problem

The inventors of the present disclosure have made efforts to find an Fc-gamma receptor mutant capable of extending the serum half-life of many peptide drugs that cannot be applied to clinical applications due to short in vivo half-life and short in vivo residence time. As a result, they have identified that the IgG binding ability of an Fc-gamma receptor can be remarkably improved as compared to the wild type through optimization by substituting a part of an amino acid sequence with a different amino acid sequence, and have completed the present disclosure.

The present disclosure is directed to providing a polypeptide including an Fc-gamma receptor mutant.

The present disclosure is also directed to providing a nucleic acid molecule encoding the polypeptide.

The present disclosure is also directed to providing a vector containing the nucleic acid molecule.

The present disclosure is also directed to providing a host cell containing the vector.

The present disclosure is also directed to providing a composition containing the polypeptide, the nucleic acid molecule or the vector.

The present disclosure is also directed to providing a composition containing the polypeptide or the nucleic acid molecule.

The present disclosure is also directed to providing a kit for detecting an IgG antibody containing the polypeptide or an Fc region of the IgG antibody.

The present disclosure is also directed to providing a fusion protein or peptide wherein the polypeptide is fused with a physiologically active protein or a physiologically active peptide.

The present disclosure is also directed to providing a method for preparing a polypeptide including an Fc-gamma receptor mutant.

The present disclosure is also directed to providing a method for identifying the presence of an IgG antibody or an Fc region of the IgG antibody contained in a sample.

The present disclosure is also directed to providing a method for purifying an IgG antibody or an Fc region of the IgG antibody contained in a sample.

The present disclosure is also directed to providing a method for screening a human Fc-gamma receptor mutant with improved binding ability to an IgG antibody or an Fc region of the IgG antibody.

Other purposes and advantages of the present disclosure will be apparent from the following detailed description, claims and drawings.

Technical Solution

In an aspect of the present disclosure, the present disclosure provides a polypeptide including an Fc-gamma receptor mutant.

The inventors of the present disclosure have made efforts to find an Fc-gamma receptor mutant capable of extending the serum half-life of many peptide drugs that cannot be applied to clinical applications due to short in vivo half-life and short in vivo residence time. As a result, they have identified that the IgG binding ability of an Fc-gamma receptor can be remarkably improved as compared to the wild type through optimization by substituting a part of an amino acid sequence with a different amino acid sequence.

In the present specification, the term "Fc-gamma receptor mutant" refers to a polypeptide of an Fc-gamma receptor which is different from the wild-type Fc-gamma receptor. The difference may include the difference in binding ability to immunoglobulins, therapeutic potential, amino acid composition, solubility, etc. Specifically, it refers to change in one or more amino acid sequence from an Fc-gamma receptor consisting of natural or synthetic amino acids, capable of binding to an immunoglobulin or an Fc region thereof (Fc region), and the change includes substitution, deletion or insertion of an amino acid.

The immunoglobulin may be any one of IgG, IgE, IgA, IgM or IgD. Specifically, it is IgG. The immunoglobulin may be derived from any animal, including human, rat, mouse, cow, sheep, goat, chicken, ostrich and camel. Specifically, it is derived from human.

According to a specific exemplary embodiment of the present disclosure, the Fc-gamma receptor mutant of the present disclosure has improved characteristics when compared with the wild-type Fc-gamma receptor.

In the present specification, the term "improved characteristics" refers to desirable characteristics when compared with the wild-type Fc-gamma receptor. The characteristics may include increased or enhanced binding ability to an immunoglobulin or an Fc region, regulation or inhibition of immune function by binding to an Fc region of an immunoglobulin, increase in the half-life of a polypeptide or a protein used as a therapeutic agent in serum, or allowing detection of a target polypeptide or protein (e.g., an immunoglobulin) or improvement of the detection accuracy.

In the present specification, the term "change in binding ability to an immunoglobulin" means that the Fc-gamma receptor mutant of the present disclosure has a different binding activity to an immunoglobulin from that of the wild-type Fc-gamma receptor. It may refer to the change in the binding ability between an immunoglobulin and the receptor, i.e., the change in the binding ability of the receptor to an immune complex, aggregate, dimer or monomer immunoglobulin when compared with that of the wild-type Fc-gamma receptor.

In the present specification, the term "change in one or more amino acid affecting the binding ability to an immunoglobulin" means the change in an amino acid region or a region of an amino acid region of an Fc-gamma receptor, associated with binding between the wild-type Fc-gamma receptor and an immunoglobulin. The change may result from substitution, deletion or insertion.

According to an exemplary embodiment of the present disclosure, the Fc-gamma receptor mutant of the present disclosure has improved binding ability to an IgG antibody or an Fc region of an IgG antibody when compared with the wild-type Fc-gamma receptor.

The Fc-gamma receptor mutant may have a binding ability improved by 10% or more, 20% or more, 30% or more, 40% or more, 50% or more, 60% or more, 70% or more, 80% or more or 90% or more when compared with the wild-type Fc-gamma receptor, or 2 times or more, 3 times or more, 4 times or more, 5 times or more, 6 times or more, 7 times or more, 8 times or more, 9 times or more, 10 times or more, 20 times or more or 30 times or more when compared with the wild-type Fc-gamma receptor (Examples 2, 8, 10, 11, 13, 15-17 and 19).

According to a specific exemplary embodiment of the present disclosure, the mutant has a binding ability to an Fc region of an IgG antibody or an IgG antibody improved by 3-fold or more when compared with the wild-type Fc-gamma receptor.

According to a specific exemplary embodiment of the present disclosure, the Fc receptor of the present disclosure is in the form of an isolated form, which means that other proteins and/or non-protein molecules are removed.

The isolated form may have a purity of at least 40% or more, specifically 60% or more, more specifically 75% or more, further more specifically 85% or more as compared to a non-Fc receptor molecule, when measured based on weight, activity, amino acid similarity, reactivity with antibodies or other existing means.

The polypeptide including the Fc receptor of the present disclosure may be bound to a cell membrane or a supporting means, or may be in a soluble form. For use as a pharmaceutical composition, the polypeptide may be specifically in a soluble form.

The polypeptide may be labeled with a reporter molecule which generates a detectable signal under an appropriate condition. The reporter molecule may be a radionucleotide, a chemiluminescent molecule, a bioluminescent molecule, a fluorescent molecule or an enzyme. Commonly used enzymes may include horseradish peroxidase, glucose oxidase, β-galactosidase, alkaline phosphatase, etc.

Specifically, the Fc receptor of the present disclosure mutant includes a natural or artificial mutant, a variant or a derivative of the amino acid of the wild-type Fc receptor. The wild-type Fc receptor on which the mutant, the variant or the derivative is based may be derived from human or an animal species. Specifically, the animal species may be a mammal such as mouse, rat, rabbit, cow, sheep, camel, goat, etc.

The amino acid change for preparing the Fc receptor of the present disclosure mutant, i.e., deletion, insertion or substitution, is achieved by an existing means. When the Fc receptor mutant is derived from a recombinant, a nucleic acid encoding the molecule may be one in which a code associated with insertion or substitution of one or more amino acid is introduced or deleted adequately. The desired amino acid sequence may be introduced when synthesizing a receptor molecule by de novo peptide synthesis.

According to a specific exemplary embodiment of the present disclosure, the mutant may be one in which the 117th amino acid and the 159th amino acid from the sequence of the wild-type Fc-gamma receptor of SEQ ID NO 43 or SEQ ID NO 49 are changed.

According to a specific exemplary embodiment of the present disclosure, the mutant is one in which the 117th amino acid, the 119th amino acid and the 159th amino acid from the sequence of the wild-type Fc-gamma receptor of SEQ ID NO 43 or SEQ ID NO 49 are changed and, additionally, one or more amino acid selected from the 86th amino acid, the 127th amino acid and the 171st amino acid is changed.

According to a specific exemplary embodiment of the present disclosure, the mutant is an Fc-gamma receptor mutant containing a sequence wherein the 117th amino acid from SEQ ID NO 43 or SEQ ID NO 49 is substituted with asparagine (N) and the 159th amino acid is substituted with glutamine (Q).

According to a specific exemplary embodiment of the present disclosure, the mutant is one in which, in addition to the substitution of the 117th amino acid and the 159th amino acid from SEQ ID NO 43 or SEQ ID NO 49, one or more amino acid selected from a group consisting of the 55th amino acid, the 86th amino acid, the 119th amino acid, the 127th amino acid and the 171st amino acid is substituted.

According to a specific exemplary embodiment of the present disclosure, the mutant is an Fc-gamma receptor mutant including a sequence wherein the 86th amino acid is substituted with aspartic acid (D), the 117th amino acid is substituted with asparagine (N), the 119th amino acid is substituted with methionine (M) or valine (V), the 127th amino acid is substituted with leucine (L), the 159th amino acid is substituted with glutamine (Q) and the 171st amino acid is substituted with glutamic acid (E) from SEQ ID NO 43 or SEQ ID NO 49.

According to a specific exemplary embodiment of the present disclosure, the mutant further includes, in addition to the substitution of the 117th amino acid and the 159th amino acid from SEQ ID NO 43 or SEQ ID NO 49, one or more amino acid substitution selected from a group consisting of substitution of the 55th amino acid with histidine (H), substitution of the 86th amino acid with aspartic acid (D), substitution of the 119th amino acid with methionine (M) or valine (V), substitution of the 127th amino acid with leucine (L) and substitution of the 171st amino acid with glutamic acid (E).

According to a specific exemplary embodiment of the present disclosure, the mutant includes a sequence of SEQ ID NO 44.

According to a specific exemplary embodiment of the present disclosure, the mutant includes a sequence of SEQ ID NO 45.

According to a specific exemplary embodiment of the present disclosure, the mutant includes a sequence of SEQ ID NO 46.

According to a specific exemplary embodiment of the present disclosure, the mutant includes a sequence of SEQ ID NO 47.

According to a specific exemplary embodiment of the present disclosure, the mutant includes a sequence of SEQ ID NO 48.

According to a specific exemplary embodiment of the present disclosure, the mutant includes a sequence of SEQ ID NO 50.

The Fc-gamma receptor mutant of the present disclosure includes various mutants of the Fc-gamma receptor (FcγRI, FcγRIIa, FcγRIIb, FcγRIIIa, etc.). Specifically, it may be an Fc-gamma IIa receptor mutant or an Fc-gamma IIb receptor mutant.

In another aspect of the present disclosure, the present disclosure provides a nucleic acid molecule encoding the polypeptide, a vector containing the nucleic acid molecule or a host cell containing the vector.

In another aspect of the present disclosure, the present disclosure provides a method for preparing a polypeptide containing an Fc-gamma receptor mutant, which includes:

a) a step of culturing a host cell containing a vector containing a nucleic acid molecule encoding the polypeptide; and b) a step of recovering a polypeptide expressed by the host cell.

The nucleic acid molecule of the present disclosure may be an isolated or recombinant one, and may include not only a single-strained or double-stranded DNA or RNA, a sequence complementary thereto. The "isolated nucleic acid" may be a nucleic acid isolated from the genetic sequence of an isolated genome of an individual when it is a nucleic acid isolated from a natural source. A nucleic acid synthesized enzymatically or chemically from a template, e.g., a PCR product, a cDNA molecule or an oligonucleotide may also be understood as an isolated nucleic acid molecule. The isolated nucleic acid molecule is a nucleic acid molecule which is a component of a fragment or a larger nucleic acid construct. The nucleic acid is "operably linked" when it is placed into a functional relationship with another nucleic acid sequence. For example, a DNA for a presequence or a secretory leader is operably linked to a DNA for a polypeptide if it is expressed as a preprotein before secretion of the polypeptide, a promoter or an enhancer is operably linked to a coding sequence if it affects the transcription of the polypeptide sequence, or a ribosome binding site is operably linked to a coding sequence if it is positioned so as to facilitate translation. Generally, "operably linked" means that the DNA sequences being linked are contiguous and, in the case of a secretory leader, contiguous and existing in the same reading frame. However, enhancers do not have to be contiguous. The linking is accomplished by ligation at convenient restriction enzyme sites. If such sites do not exist, a synthetic oligonucleotide adapter or a linker is used in accordance with conventional practice.

In the present specification, the term "vector" refers to a carrier capable of inserting a nucleic acid sequence for introduction of the nucleic acid sequence into a cell which can replicate it. The nucleic acid sequence can be exogenous or heterologous. The vector may be a plasmid, a cosmid or a virus (e.g., bacteriophage), although not being limited thereto. Those skilled in the art can construct the vector according to a standard recombination technology (Maniatis, et al., *Molecular Cloning*, A Laboratory Manual, Cold Spring Harbor Press, Cold Spring Harbor, N.Y., 1988; Ausubel et al., In: *Current Protocols in Molecular Biology*, John, Wiley & Sons, Inc, N Y, 1994; etc.).

In the present specification, the term "expression vector" refers to a vector containing a nucleic acid sequence encoding at least a part of a transcribed gene product. In some cases, the RNA molecule is translated later into a protein, a polypeptide or a peptide. The expression vector may contain various regulatory sequences. The vector or the expression vector may contain, together with a regulatory sequence controlling transcription and translation, other nucleic acid sequences providing different functions.

In the present specification, the term "host cell" includes both a eukaryotic cell and a prokaryotic cell, and refers to a transformable cell of any organism that can replicate the vector or can express a gene coded by the vector. The host cell can be transfected or transformed by the vector, which means a process whereby an exogenous nucleic acid molecule is transferred or introduced into the host cell.

In another aspect of the present disclosure, the present disclosure provides a method for identifying the presence of an IgG antibody or an Fc region of the IgG antibody contained in a sample, which includes:

a) a step of preparing a sample for identifying the presence of an IgG antibody or an Fc region of the IgG antibody;

b) a step of binding the polypeptide described above to the sample by mixing them together; and c) a step of identifying the presence of the IgG antibody or the Fc region of the IgG antibody with the polypeptide bound.

In another aspect of the present disclosure, the present disclosure provides a method for purifying an IgG antibody or an Fc region of the IgG antibody contained in a sample, which includes:

a) a step of binding the polypeptide described above to a sample containing an IgG antibody or an Fc region of the IgG antibody by mixing them together; and b) a step of purifying the IgG antibody or the Fc region of the IgG antibody with the polypeptide bound.

A described above, because the Fc-gamma receptor mutant of the present disclosure has improved binding ability to an IgG antibody or an Fc region of the IgG antibody when compared with the wild-type Fc-gamma receptor, it can be usefully used to identify the presence of, detect or purify the IgG antibody or the Fc region of the IgG antibody.

The separation and purification of the polypeptide can be conducted by any of several known technologies. Examples include ion-exchange chromatography, gel permeation chromatography, affinity chromatography, high-performance liquid chromatography (HPLC), reversed-phase high-performance liquid chromatography and preparative disc gel electrophoresis, but are not limited thereto. The polypeptide separation and purification technology may require modification of a polypeptide according to a common method. For example, a histidine tag may be added to a protein during nickel column purification. Other modifications may induce higher or lower activity, allow more protein production or simply purification of proteins. Other tags may include a FLAG-tag. Specifically, the tag is used in a eukaryotic host.

Methods for purifying polypeptides include the ammonium sulfate precipitation method of purifying proteins based on the change in solubility. This method is more specific than general techniques such as salting out. Ammonium sulfate is generally used because it has high solubility and allows a salt solution with high ionic strength. The solubility of a polypeptide varies according to the ionic strength of the solution, thus according to the salt concentration.

Because the solubility of a polypeptide is distinctly different at high ionic strength, salting out is a very useful method helpful in purification of specific polypeptides. Specifically, by the addition of kosmotropic ammonium sulfate, not only folding byproducts such as unfolded and misfolded species but also host cell-derived impurities like cell wall components and polypeptides are precipitated. Because precipitation efficiency increases with the increasing precipitant concentration, a highly purified Fc receptor mutant product may be obtained while the Fc receptor mutant is resistant to precipitation at such high ammonium sulfate concentrations.

The precipitated polypeptide is removed by centrifugation, and the concentration of the precipitated polypeptide of interest is increased while the polypeptide byproducts remain in the solution. Then, the precipitated polypeptide of interest is recovered by centrifugation and dissolved in a fresh buffer for purification.

In another aspect of the present disclosure, the present disclosure provides a method for screening an Fc-gamma receptor mutant with improved binding ability for an IgG antibody or an Fc region of the IgG antibody, which includes:

a) a step of establishing an Fc-gamma receptor mutant library including a sequence wherein the 117th amino acid from SEQ ID NO 43 or SEQ ID NO 49 is substituted with asparagine (N) and the 159th amino acid is substituted with glutamine (Q); and b) a step of screening an Fc-gamma receptor mutant with improved binding ability for an IgG antibody or an Fc region of the IgG antibody when compared with the Fc-gamma receptor mutant including only the substitution of the two amino acid sequences from the library.

In another aspect of the present disclosure, the present disclosure provides a method for screening an Fc-gamma receptor mutant with improved binding ability for an IgG antibody or an Fc region of the IgG antibody, which includes:

a) a step of establishing an Fc-gamma receptor mutant library including a sequence wherein the 117th amino acid is substituted with asparagine (N) and the 159th amino acid is substituted with glutamine (Q) from SEQ ID NO 43 or SEQ ID NO 49 and further including substitution of one or more amino acid selected form a group consisting of the 86th amino acid, the 127th amino acid and the 171st amino acid; and b) a step of screening an Fc-gamma receptor mutant with improved binding ability for an IgG antibody or an Fc region of the IgG antibody when compared with the Fc-gamma receptor mutant including only the substitution of the two amino acid sequences of the 117th and 159th amino acids from the library.

In another aspect of the present disclosure, the present disclosure provides a method for screening an Fc-gamma receptor mutant with improved binding ability for an IgG antibody or an Fc region of the IgG antibody, which includes:

a) a step of establishing an Fc-gamma receptor mutant library including a sequence wherein the 55th amino acid is substituted with histidine (H), the 117th amino acid is substituted with asparagine (N), the 119th amino acid is substituted with valine (V), the 159th amino acid is substituted with glutamine (Q) and the 171st amino acid is substituted with glutamic acid (E) from SEQ ID NO 43 or SEQ ID NO 49; and b) a step of screening an Fc-gamma receptor mutant with improved binding ability for an IgG antibody or an Fc region of the IgG antibody when compared with the Fc-gamma receptor mutant including only the substitution of the five amino acid sequences of the 55th, 117th, 119th, 159th and 171st amino acids from the library.

The screening method of the present disclosure may be usefully used to screen an Fc-gamma receptor mutant with improved binding ability for an IgG antibody or an Fc region of the IgG antibody when compared with the Fc-gamma receptor mutant.

The mutant screened according to the screening method of the present disclosure may further include the following amino acid changes: substitution of one or more amino acid selected from a group consisting of the 55th amino acid, the 86th amino acid, the 119th amino acid, the 127th amino acid and the 171st amino acid from SEQ ID NO 43 or SEQ ID NO 49.

According to a specific exemplary embodiment of the present disclosure, there may further be one or more amino acid substitution selected from a group consisting of substitution of the 55th amino acid with histidine (H), substitution of the 86th amino acid with aspartic acid (D), substitution of the 119th amino acid with methionine (M) or valine (V), substitution of the 127th amino acid with leucine (L) and substitution of the 171st amino acid with glutamic acid (E).

According to an exemplary embodiment of the present disclosure, an Fc-gamma receptor mutant with improved binding ability to an IgG antibody or an Fc region of the IgG antibody was screened through the screening method described above (Examples 7 and 8).

In the screening method of the present disclosure, fluorescence-activated cell sorting (FACS) or other automated flow cytometry techniques may be used. Instruments for flow cytometry are known to those skilled in the art. Examples of the instruments include FACSAria, FACS Star Plus, FACScan and FACSort (Becton Dickinson, Foster City, Calif.), Epics C (Coulter Epics Division, Hialeah, Fla.), MOFLO (Cytomation, Colorado Springs, Colo.) and MOFLO-XDP (Beckman Coulter, Indianapolis, Ind.). In general, separation of cells and other particles in a liquid sample is included in the flow cytometry technique. Typically, the purpose of flow cytometry is to analyze one or more characteristics of separated particles (e.g., the presence of labeled ligands or other molecules). The particles are sorted based on size, refraction, light scattering, opacity, roughness, shape, fluorescence, etc. as they pass through a sensor one by one.

In another aspect of the present disclosure, the present disclosure provides a composition containing the polypeptide, the nucleic acid molecule or the vector described above.

According to a specific exemplary embodiment of the present disclosure, the composition of the present disclosure is for detecting an IgG antibody or an Fc region of the IgG antibody contained in a sample.

In the present specification, the term "sample" refers to a substance likely to contain an IgG antibody or an Fc region of the IgG antibody. The sample may be excrements, cells, blood, plasma, serum, hair, urine, etc. isolated naturally or artificially from a subject.

The term "subject" used in the present specification includes a mammal including a primate such as human and chimpanzee, a pet such as dog, cat, etc., a cattle such as cow, horse, sheep, goat, etc., and a rodent such as mouse, rat, etc.

In addition, the composition may be contained in a kit which may be usefully used to detect an IgG antibody or an Fc region of the IgG antibody contained in a sample, quantify the amount of the IgG antibody in a subject or measure or detect the immunity-related condition of a patient (e.g., immunological changes caused by immune hypersensitivity, autoimmune disease or organ transplantation).

In another aspect of the present disclosure, the present disclosure provides a fusion protein or peptide wherein the polypeptide is bound to a physiologically active protein or a physiologically active peptide.

The fusion protein or peptide according to the present disclosure has increased in vivo half-life because the physiologically active protein or the physiologically active peptide is bound to the Fc-gamma receptor mutant and thus can be retained longer in vivo.

In the present specification, the term "fusion protein (fusion polypeptide)" may refer to a fusion protein with a new molecular structure wherein one or more protein having physiological activity is bound to the N-terminal or C-terminal of the Fc-gamma receptor mutant. And, the "fusion peptide" refers to a fusion peptide with a new molecular structure wherein one or more low-molecular-weight peptide having physiological activity is bound to the N-terminal or C-terminal of the Fc-gamma receptor mutant.

The physiologically active protein or the physiologically active peptide may be bound to the Fc-gamma receptor mutant directly or via a linker composed of amino acids.

Specifically, the physiologically active protein or the physiologically active peptide may be bound to the Fc-gamma receptor mutant using a known genetic recombination technology. It may be bound to the N-terminal, the C-terminal or a free radical of the Fc-gamma receptor mutant using a known crosslinker.

The physiologically active protein may include a hormone and a receptor thereof, a biological response modifier and a receptor thereof, a cytokine and a receptor thereof, an enzyme, an antibody, an antibody fragment, etc. Specifically, the physiologically active protein may include human growth hormone (hGH), insulin, follicle-stimulating hormone (FSH), human chorionic gonadotropin, parathyroid hormone (PTH), erythropoietin (EPO), thrombopoietin (TPO), granulocyte colony-stimulating factor (G-CSF), granulocyte-macrophage colony-stimulating factor (GM-CSF), interferon-alpha, interferon-beta, interferon-gamma, interleukin, macrophage-activating factor, tumor necrosis factor, tissue plasminogen activator, blood coagulation factor VII, VIIa, VIII, IX, hBMP2 (human bone morphogenic protein 2), KGF (keratinocyte growth factor), PDGF (platelet-derived growth factor), glucocerebrosidase, α-galactosidase A, α-L-iduronidase, iduronate-2-sulfatase, lactase, adenosine deaminase, butyrylcholinesterase, chitinase, glutamate decarboxylase, imiglucerase, lipase, uricase, platelet-activating factor acetylhydrolase, neutral endopeptidase, urokinase, streptokinase, myeloperoxidase, superoxide dismutase, botulinum toxin, collagenase, hyaluronidase, L-asparaginase, a monoclonal antibody, a polyclonal antibody, scFv, Fab, Fab', F(ab')2, Fd, etc., although not being limited thereto.

The physiologically active peptide may include glucagon-like peptide-1 (GLP-1) and an analogue thereof, exendin and an analogue thereof, somatostatin and an analogue thereof, LHRH (luteinizing hormone-releasing hormone) agonist and antagonist, adrenocorticotropic hormone, growth hormone-releasing hormone, oxytocin, thymosin alpha-1, corticotropin-releasing factor, calcitonin, bivalirudin, a vasopressin analogue, a fragment of a physiologically active protein, etc., although not being limited thereto.

The peptide of the present disclosure may be usefully used to increase the in vivo half-life of another physiologically active protein or peptide. The fusion protein or peptide may have increased in vivo half-life due to increased retention in vivo.

According to a specific exemplary embodiment of the present disclosure, the composition of the present disclosure is a pharmaceutical composition for immunosuppression.

The pharmaceutical composition of the present disclosure may contain: (a) the polypeptide, a nucleic acid molecule encoding the same or a vector containing the nucleic acid molecule; and (b) a pharmaceutically acceptable carrier.

According to a specific exemplary embodiment of the present disclosure, the composition of the present disclosure is a pharmaceutical composition for suppressing organ transplant rejection or for preventing or treating autoimmune disease.

In another aspect of the present disclosure, the present disclosure provides a method for suppressing immunity or organ transplant rejection, which includes a step of administering the pharmaceutical composition.

In another aspect of the present disclosure, the present disclosure provides a method for preventing or treating autoimmune disease, which includes a step of administering the pharmaceutical composition.

In the present specification, the term "autoimmune disease" is used interchangeably with "autoimmune disorder" and refers to a condition arising from an abnormal immune response to one's own cells, tissues or organs. The term "inflammatory disease" is used interchangeably with the term "inflammatory disorder" and refers to a condition characterized by inflammation, specifically chronic inflammation. Autoimmune disease may or may not be related with inflammation. In addition, inflammation may or may not cause autoimmune disease.

Examples of autoimmune disease that may be prevented or treated by the pharmaceutical composition of the present disclosure include alopecia areata, ankylosing spondylitis, antiphospholipid syndrome, Addison's disease, autoimmune disease of the adrenal gland, autoimmune hemolytic anemia, autoimmune hepatitis, autoimmune ovaritis and testitis, autoimmune thrombocytopenia, Bechet's disease, bullous pemphigoid, cardiomyopathy, celiac sprue-dermatitis, atopic dermatitis, asthma, rhinitis, chronic fatigue immune dysfunction syndrome, chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre Syndrome, Hashimoto's thyroiditis, idiopathic pulmonary fibrosis, idiopathic thrombocytopenic purpura, IgA neuritis, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis nodosa, polychondritis, autoimmune polyendocrine syndrome, polymyalgia rheumatica, polymyositis, dermatomyositis, primary hyperaldosteronism, primary biliary cirrhosis, psoriasis, psoriatic arthritis, Raynaud's phenomenon, Reiter's syndrome, rheumatoid arthritis, sarcoidosis, dermatosclerosis, stiff-person syndrome, systemic lupus erythematosus, lupus erythematosus, Takayasu's arteritis, temporal arteritis, giant-cell arteritis, ulcerative colitis, uveitis, leukoderma and Wegener's granulomatosis, although not being limited thereto.

The pharmaceutically acceptable carrier contained in the pharmaceutical composition of the present disclosure is a commonly used one and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain, in addition to the above-described ingredients, a lubricant, a humectant, a sweetener, a flavorant, an emulsifier, a suspending agent, a preservative, etc. Suitable pharmaceutically acceptable carriers and preparations are described in detail in Remington's Pharmaceutical Sciences (19th ed., 1995).

The pharmaceutical composition of the present disclosure may be administered orally or parenterally, specifically parenterally, for example, via intravenous injection, topical injection, intraperitoneal injection, etc.

An adequate administration dosage of the pharmaceutical composition of the present disclosure varies depending on such factors as formulation method, administration method, the age, body weight and sex of a patient, pathological condition, diet, administration time, administration route, excretion rate and response sensitivity. An ordinarily trained physician may easily determine and prescribe an administration dosage effective for the desired treatment or prevention. According to a specific exemplary embodiment of the present disclosure, a daily administration dosage of the pharmaceutical composition of the present disclosure is 0.0001-100 mg/kg.

The pharmaceutical composition of the present disclosure may be formulated according to a method that may be easily carried out by those of ordinary skill in the art into single-dose forms or a multi-dose packages using a pharmaceutically acceptable carrier and/or excipient. The formulation may be a solution in an oil or aqueous medium, a suspension, an emulsion, an extract, a powder, a granule, a tablet or a capsule, and may further contain a dispersant or a stabilizer.

The pharmaceutical composition of the present disclosure may be used either alone or in combination with other common chemotherapy or biological therapy. The immune-related disease may be treated more effectively by the combination therapy.

Advantageous Effects

The features and advantages of the present disclosure may be summarized as follows:

(i) The present disclosure provides a polypeptide including an Fc-gamma receptor mutant.

(ii) The present disclosure also provides a method for preparing the polypeptide.

(iii) The Fc-gamma receptor mutant of the present disclosure is optimized by substituting a part of an amino acid sequence of the Fc-gamma receptor with a different amino acid sequence, so as to provide an excellent selective binding ability to immunoglobulins. Therefore, it can be usefully used for increasing in vivo half-life of drugs, detecting and purifying immunoglobulins, inhibiting organ transplant rejections, or preventing or treating autoimmune diseases.

Figure 1:
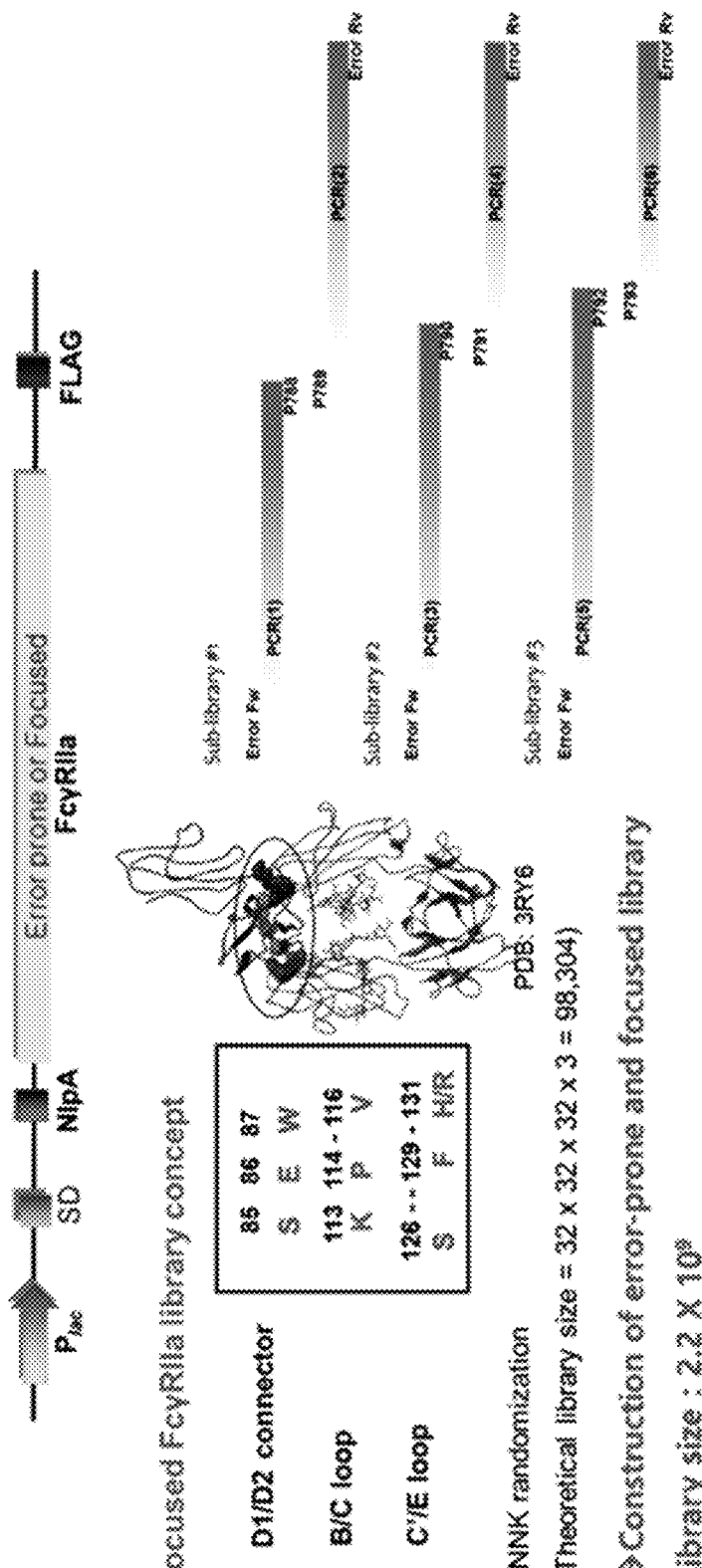
FIG. 1 schematically illustrates the establishment of an FcγRIIa mutant library of the present disclosure.

FIG. 6 shows a result of investigating the activity of SH2A40 by performing ELISA.

FIG. 7 schematically illustrates a process of establishing an FcγRIIa mutant library with no N-linked canonical glycosylation motif formed.

FIG. 8 compares the binding ability of mutants screened using an established library and flow cytometry (MG2A28 and MG2A45) for Fc.

FIG. 9 shows a result of purifying screened mutants.

FIG. 10 shows an ELISA result of investigating the binding ability of screened mutants for Fc.

FIG. 11 shows a result of measuring the $K_D$ values of Fc-gamma receptor mutants and rituximab by biolayer interferometry.

FIG. 12 compares the affinity of mutants screened using an established library and flow cytometry (MG2A28 and MG2A45) for Fc.

FIG. 13 shows a result of purifying screened mutants.

FIG. 14 shows an ELISA result of investigating the binding ability of screened mutants for Fc.

FIG. 15 shows a result of measuring the $K_D$ values of Fc-gamma receptor mutants and rituximab by biolayer interferometry.

FIG. 16 shows an ELISA result of investigating the binding ability of Fc-gamma receptor mutants to mouse serum IgG.

FIG. 17 shows a result of comparing the affinity of wild-type FcγRIIb and MG2A45.1 mutation-introduced FcγRIIb (MG2B45.1) for human serum IgG-FITC.

FIG. 18 shows bevacizumab scFv, bevacizumab scFv-FcγRIIa wild type and bevacizumab scFv-MG2A45.1 expressed in mammalian cells.

FIG. 19 shows an ELISA assay result of analyzing the VEGF binding activity of bevacizumab scFv, bevacizumab scFv-FcγRIIa wild type and bevacizumab scFv-MG2A45.1 for bevacizumab scFv.

FIG. 20 shows an ELISA assay result of analyzing the IgG1 Fe (rituximab) binding activity of bevacizumab scFv, bevacizumab scFv-FcγRIIa wild type and bevacizumab scFv-MG2A45.1 for FcγRIIa.

BEST MODE

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1. Construction of FcγRIIa Mutant Library

Random mutation-introduced FcγRIIa genes were prepared using MJ #160 and MJ #161 primers based on the pMopac12-NlpA-FcγRIIa-FLAG vector so that about 0.2% of random mutation occurred in FcγRIIa. In addition, focused inserts with various amino acids introduced were prepared by introducing the degenerate codon NNK at the IgG Fc binding site of FcγRIIa using MJ #160, MJ #161, p788, p789, p790, p791, p792 and p793 primers (Table 1). The prepared two inserts were treated with the SfiI (New England Biolab) restriction enzyme and ligated with the vector. Then, an FcγRIIa mutant library (library size: 2.2× $10^9$) was constructed by transforming into *E. coli* Jude1 ((F' [Tn10(Tet$^r$)proAB$^+$lacI$^q$Δ(lacZ)M15] mcrAΔ(mrr-hs-dRMS-mcrBC)Φ80dlacZΔM15 ΔlacX74 deoR recA1 araD139Δ(ara leu)7697 galUgalKrpsLendAInupG) (FIG. 1).

TABLE 1

| Primer # | Sequence (5'→3') |
| --- | --- |
| P788 (SEQ ID NO 1) | GCGGGGTTTGCAGCACCAGMNNMNNMNNAAGCACGGTCAGATGCACCG |
| P789 (SEQ ID NO 2) | CGGTGCATCTGACCGTGCTTNNKNNKNNKCTGGTGCTGCAAACCCCGC |
| P790 (SEQ ID NO 3) | GCTTTTGCCATTCTGAAAAAGGTCACTTTMNNCAGMNNMNNATCTTTCCAGCTATGGCAACGCAG |
| P791 (SEQ ID NO 4) | CTGCGTTGCCATAGCTGGAAAGATNNKNNKCTGNNKAAAGTGACCTTTTTTCAGAATGGCAAAAGC |
| P792 (SEQ ID NO 5) | GCGGAATGCTAAAGGTCGGATCCAGMNNAGAMNNTTTCTGMNNTTTGCCATTCTGAAAAAGGTCACTTTCACC |
| P793 (SEQ ID NO 6) | GGTGAAAGTGACCTTTTTTCAGAATGGCAAANNKCAGAAANNKTCTNNKCTGGATCCGACCTTTAGCATTCCGC |
| IIa Fw NdeI (SEQ ID NO 7) | GCGGAATTCCATATGCAGGCTGCCCCACCGAAAG |
| IIa Rv HindIII (SEQ ID NO 8) | TAAGGGAAGCTTAATCACGCCCATCGGTGAGC |
| MJ#1 (SEQ ID NO 9) | CCA GGC TTT ACA CTT TAT GC |
| MJ#2 (SEQ ID NO 10) | CTG CCC ATG TTG ACG ATT G |
| MJ#112 (SEQ ID NO 11) | CAGCGGTTTATCTTTCCAGCTATGGC |
| MJ#113 (SEQ ID NO 12) | GCCATAGCTGGAAAGATAAACCGCTGNNKNNGGTGNNKTTTTTTCAGAATGGCAAAAGCCAGAAATTTTCTC |
| MJ#114 (SEQ ID NO 13) | GCCATAGCTGGAAAGATAAACCGCTGNNKGATGTGNNKTTTTTTCAGAATGGCAAAAGCCAGAAATTTTCTC |
| MJ#115 (SEQ ID NO 14) | GCCATAGCTGGAAAGATAAACCGCTGNNKTTTGTGNNKTTTTTTCAGAATGGCAAAAGCCAGAAATTTTCTC |
| MJ#116 (SEQ ID NO 15) | GCCATAGCTGGAAAGATAAACCGCTGNNKCATGTGNNKTTTTTTCAGAATGGCAAAAGCCAGAAATTTTCTC |
| MJ#117 (SEQ ID NO 16) | GCCATAGCTGGAAAGATAAACCGCTGNNKATTGTGNNKTTTTTTCAGAATGGCAAAAGCCAGAAATTTTCTC |
| MJ#118 (SEQ ID NO 17) | GCCATAGCTGGAAAGATAAACCGCTGNNKTATGTGNNKTTTTTTCAGAATGGCAAAAGCCAGAAATTTTCTC |
| MJ#119 (SEQ ID NO 18) | GCCATAGCTGGAAAGATAAACCGCTGNNKNNGGTGNWKTTTTTTCAGAATGGCAAAAGCCAGAAATTTTCTC |
| MJ#120 (SEQ ID NO 19) | GCCATAGCTGGAAAGATAAACCGCTGNNKNNKGTGGCGTTTTTTCAGAATGGCAAAAGCCAGAAATTTTCTC |
| MJ#121 (SEQ ID NO 20) | GCCATAGCTGGAAAGATAAACCGCTGNNKNNKGTGGGCTTTTTTCAGAATGGCAAAAGCCAGAAATTTTCTC |
| MJ#122 (SEQ ID NO 21) | GCCATAGCTGGAAAGATAAACCGCTGNNKNNKGTGCCGTTTTTTCAGAATGGCAAAAGCCAGAAATTTTCTC |

TABLE 1-continued

| Primer # | Sequence (5'→3') |
|---|---|
| MJ#123 (SEQ ID NO 22) | GCCATAGCTGGAAAGATAAACCGCTGNNKNNKGTGCGTTTTTTTCAGAATGGCAAAAGCCAGAAATTTTCTC |
| MJ#124 (SEQ ID NO 23) | GCCATAGCTGGAAAGATAAACCGCTGNNKNNKGTGTGGTTTTTTCAGAATGGCAAAAGCCAGAAATTTTCTC |
| MJ#160 (SEQ ID NO 24) | CGCAGCGAGAGGCCCAGCCGGCCATG |
| MJ#161 (SEQ ID NO 25) | CGCAATTCGGCCCCCGAGGCCCC |
| MJ#162 (SEQ ID NO 26) | CGCAGCGAGCGCGCACTCCATGCAGGCTGCCCCACC |
| MJ#163 (SEQ ID NO 27) | CCCTAAAATCTAGAAATCACGCCCATCGGTGAGC |
| MJ#197 (SEQ ID NO 28) | CGGGAAAATTTCTTGGATTTTCCATTCTGGAAGAA |
| MJ#198 (SEQ ID NO 29) | GCTGGAAGGACAAGCCTCTGGTCAATGTCGTGTTCTTCCAGAATGGAAAATCCAAGAAATTTTCCCG |
| MJ#199 (SEQ ID NO 30) | CGCAATTCGGCCCCCGAGGCCCCGGGCTCTTGGACAGTGATGGTCACAGGCTTG |
| MJ#200 (SEQ ID NO 31) | CAGCCCAGCTACCATTTCAAGGCCAAC |
| MJ#201 (SEQ ID NO 32) | GTTGGCCTTGAAATGGTAGCTGGGCTG |
| MJ#202 (SEQ ID NO 33) | CATAGGCTACACGCAGTACTCATCCAAGC |
| MJ#203 (SEQ ID NO 34) | GCTTGGATGAGTACTGCGTGTAGCCTATG |

Figure 2:
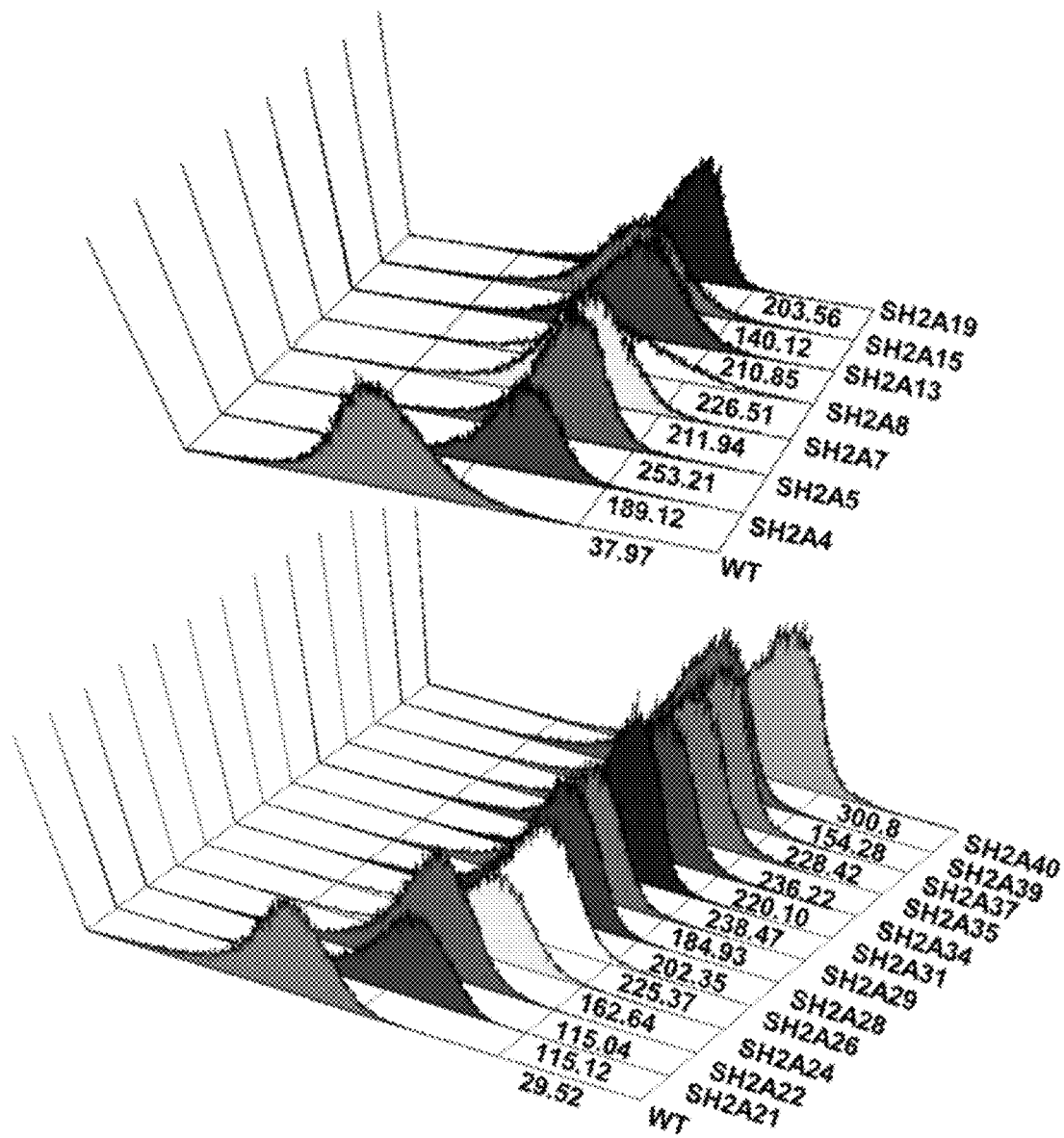
FIG. 2 shows a process of screening an SH2A40 mutant exhibiting high affinity for human serum IgG.

Example 2. Screening of FcγRIIa Mutant Library Through Bacterial Culture and Flow Cytometry 1 mL of the established FcγRIIa mutant library cells were cultured for 4 hours in a Terrific broth (TB) medium containing 2% (w/v) glucose and chloramphenicol (40 μg/mL) under the condition of 37° C. while shaking at 250 rpm. The cultured library cells were inoculated to a TB medium at 1:100 and then cultured to $OD_{600}$ 0.6 at 37° C. while shaking at 250 rpm. Then, after culturing at 25° C. for 20 minutes for cooling, 1 mM isopropyl-1-thio-β-D-galactopyranoside (IPTG) was added to induce expression. After the culturing was completed, the cells were recovered and centrifuged at 14,000 rpm for 1 minute through $OD_{600}$ normalization. After harvesting, the cells were resuspended by adding 1 mL of 10 mM Tris-HCl (pH 8.0) and centrifuged for 1 minute. This washing process was repeated twice. After resuspending in 1 mL of STE [0.5 M sucrose, 10 mM Tris-HCl, 10 mM EDTA (pH 8.0)], the outer cell membrane was removed by rotating at 37° C. for 30 minutes. After centrifuging and discarding the supernatant, the remainder was resuspended by adding 1 mL of solution A [0.5 M sucrose, 20 mM $MgCl_2$, 10 mM MOPS, pH 6.8] and then centrifuged. After resuspending in 1 mL of a mixture solution prepared by 1 mL of solution A and 20 μL of a 50 mg/mL lysozyme solution, the peptidoglycan layer was removed by rotating at 37° C. for 15 minutes. After centrifuging and removing the supernatant, the remainder was resuspended in 1 mL PBS. 300 μL of the resulting solution was taken, combined with 700 μL of PBS and a human serum IgG-FITC probe (Sigma Aldrich), and then labeled with the fluorescent probe in spheroplasts by rotation at room temperature. After the labeling, followed by washing once with 1 mL of PBS, the top 3% cells exhibiting high fluorescence were recovered by flow cytometry (S3 cell sorter; Bio-Rad) and the sorted cells were sorted again to increase purity. After amplifying genes by PCR from the resorted sample using MJ #160 and MJ #161 primers and Taq polymerase (Biosesang), a gene-amplified sub-library was constructed by ligation with SfiI restriction enzyme treatment and transformation. After repeating this procedure for a total of 4 rounds, SH2A40 mutants (SEQ ID NOS 36 and 44) showing higher affinity for human serum IgG than wild-type FcγRIIa (SEQ ID NOS 35 and 43) were screened by analyzing the 40 individual clones (FIG. 2).

Figure 3:
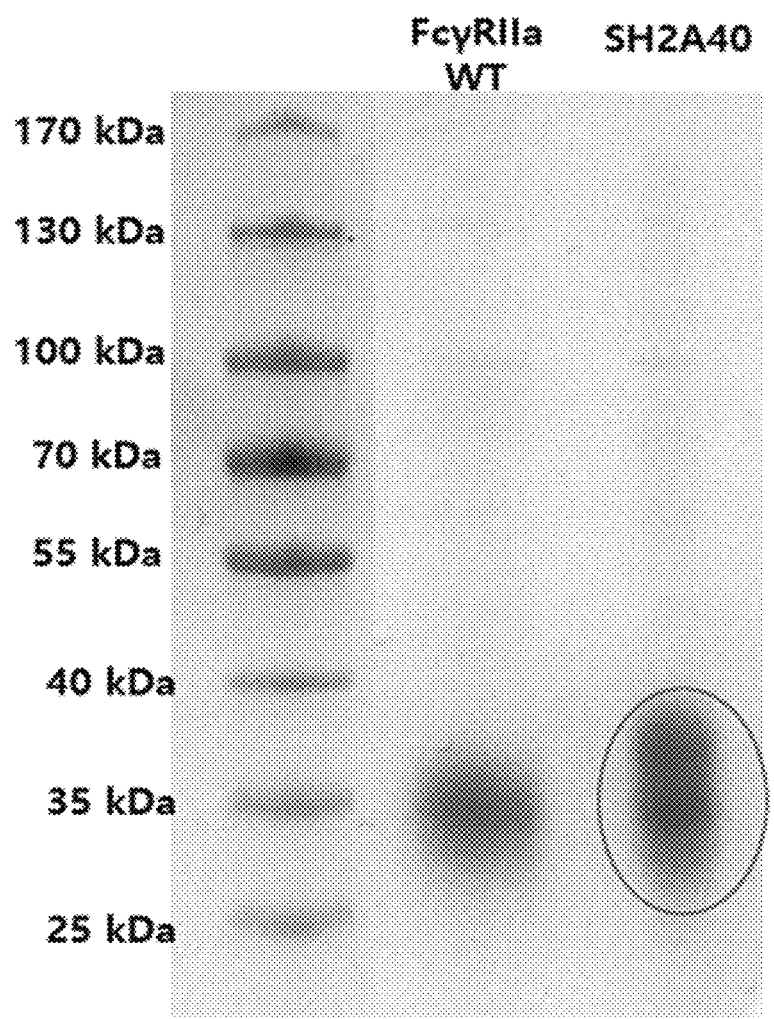
FIG. 3 shows a result showing that an FcγRIIa protein (32 kDa) has been purified with high purity on SDS-PAGE.

Example 3: Cloning, Expression and Purification of Isolated SH2A40 Mutant for Expression in Mammalian Cells In order to express the screened SH2A40 mutant in HEK293F cells, pMAZ-FcγRIIa (wild type) and pMAZ-FcγRIIa mutant (SH2A40) were prepared by gene amplification by PCR using Vent polymerase and MJ #162 and MJ #163 primers, followed by ligation by treatment with BssHII and XbaI (New England Biolab) restriction enzymes. The genes cloned into the mammalian cell expression vector pMAZ were transfected into HEK293F cells and expressed temporarily at a scale of 300 mL. After culturing was completed, the cells were removed by centrifuging at 2,000 rpm for 10 minutes, and the supernatant was taken and equilibrated using 25×PBS. The resulting solution was filtered through a 0.2-μm bottle top filter (Merck Millipore). After adding 1 mL of a Ni-NTA agarose (Qiagen) slurry equilibrated with PBS, the solution was stirred at 4° C. for 16 hours and then flown into a polypropylene column (Thermo Fisher Scientific). The pass-through solution was taken, bound to a resin and then washed sequentially with 50 mL of 1×PBS, 25 mL of 10 mM imidazole buffer, 25 mL of 20 mM imidazole buffer and 200 μL of 250 mM imidazole buffer. Elution was performed with 2.5 mL of 250 mM imidazole buffer. The collected protein was concentrated with Amicon Ultra-4 (Merck Millipore) and purified by SDS-PAGE (Bio-Rad) (FIG. 3). It was confirmed that the FcγRIIa protein (32 kDa) was purified with high purity on SDS-PAGE.

Figure 4:
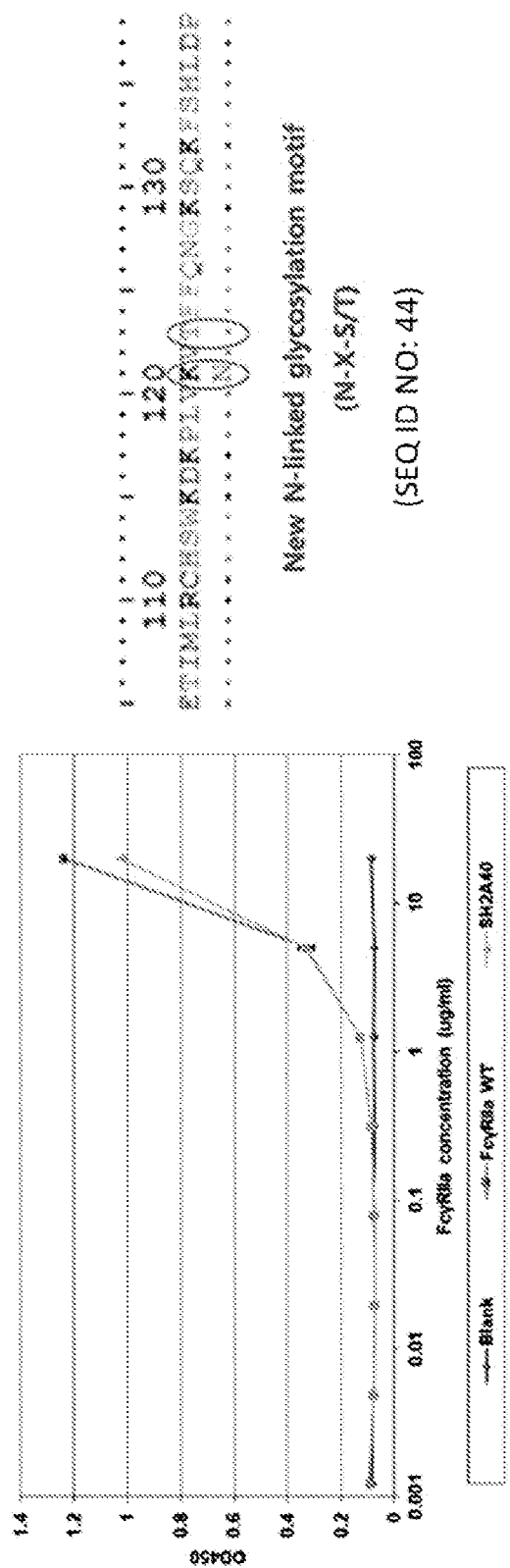
FIG. 4 compares the binding ability of SH2A40 with an N-linked canonical glycosylation motif added for Fc (SEQ ID NO 44).

Example 4: ELISA Using Rituximab Consisting of IgG1 Subclass for Analysis of Activity and Binding Ability of FcγRIIa Protein Produced Through Mammalian Cell Culturing 50 μL of rituximab diluted to 4 μg/mL with 0.05 M $Na_2CO_3$ (pH 9.6) was immobilized onto a Flat Bottom Polystyrene High Bind 96 well microplate (Costar) at 4° C. for 16 hours and then blocked in 100 μL of 5% BSA (in 0.05% PBST) at room temperature for 2 hours. After washing with 180 μL of 0.05% PBST for 4 times, 50 μL of FcγRIIa proteins serially diluted with a blocking solution were added to each well and incubated at room temperature for 1 hour. After the washing, antibody reaction was conducted using 50 μL of anti-His-HRP conjugate (Sigma-Aldrich) at room temperature for 1 hour and washing was conducted. After color development by adding 50 μL of 1-Step Ultra TMB-ELISA substrate solution (Thermo Fisher Scientific), the reaction was terminated by adding 50 μL of 2 M $H_2SO_4$. Then, analysis was conducted using the Epoch microplate spectrophotometer (BioTek). All the experiments were conducted in duplicates. Through ELISA, the binding ability for the Fc region of rituximab and wild-type FcγRIIa, SH2A40 could be compared and analyzed. SH2A40 (SEQ ID NO 44) showed a binding ability similar to that of WT FcγRIIa because a N-linked canonical glycosylation motif was newly generated (FIG. 4).

Figure 5:
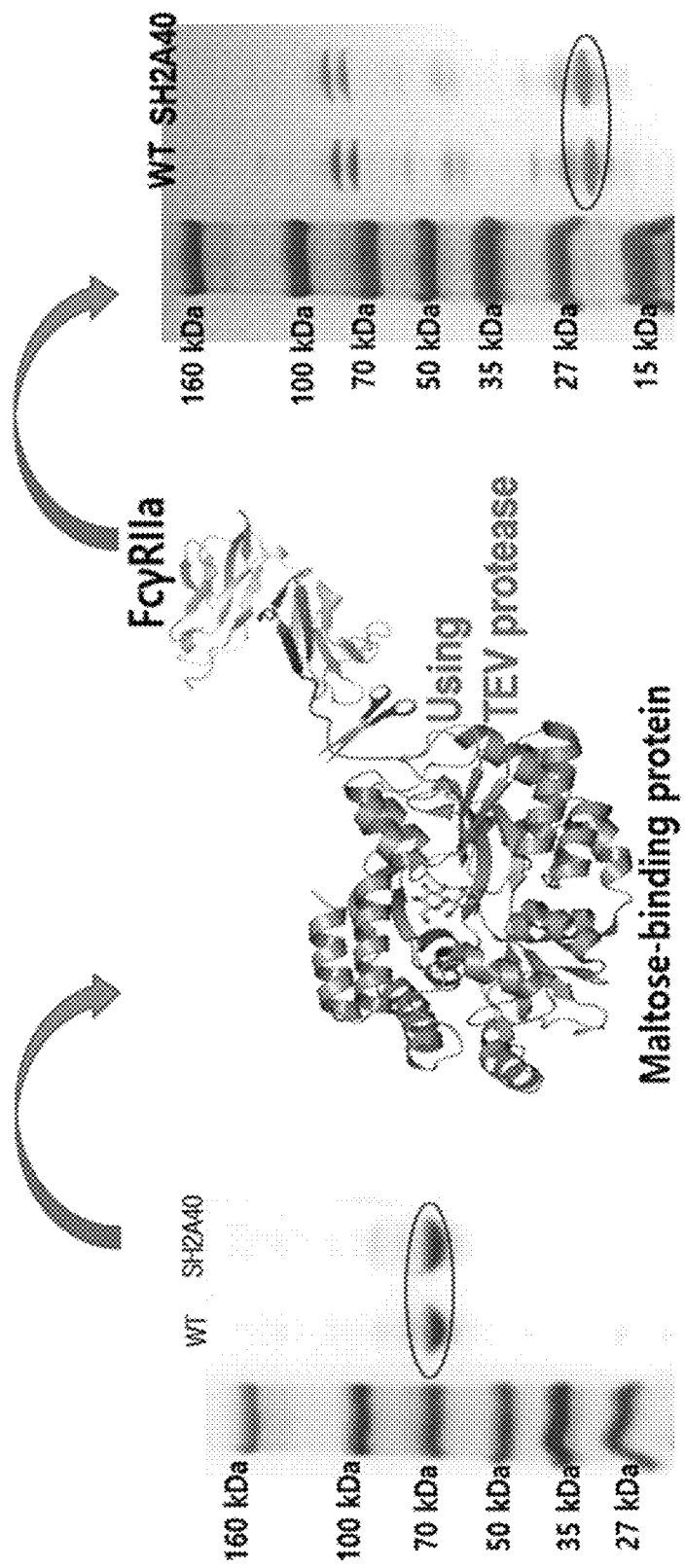
FIG. 5 schematically illustrates a process of obtaining purified SH2A40.

Example 5. Cloning for Expression of MBP-FcγRIIa Protein, Expression in *E. coli*, and Purification In order to produce the screened SH2A40 as a soluble protein, PCR was conducted using IIa_Fw_NdeI and IIa_Rv_HindIII primers. After treating with NdeI and HindIII (New England Biolab) and ligating with the pET22b-MBP-TEV site-His vector, the product was transformed into BL21 (DE3) cells. The cells were precultured in a TB medium containing 2% (w/v) glucose and ampicillin (100 μg/mL) at 37° C. while shaking at 250 rpm. The cultured cells were inoculated into a TB medium at 1:100 and then cultured until $OD_{600}$ 0.6 at 37° C. while shaking at 250 rpm. Subsequently, after culturing the cells at 18° C. for 20 minutes for cooling, expression was induced for 14 hours by adding 1 mM IPTG. After the culturing was finished, the cells were harvested by centrifuging at 7,000 rpm for 10 minutes. The cells were sonicated (5 seconds on/10 seconds off, 100 cycles) for lysis and centrifuged at 15,000 rpm for 30 minutes. The supernatant was filtered through a 0.45-μm syringe filter. The filtered supernatant was bound to a Ni-NTA resin, washed with 100 mL of 10 mM imidazole buffer and 100 mL of 20 mM imidazole buffer, and then eluted with 4 mL of 50 mM imidazole buffer. The eluted sample was buffer-exchanged with 50 mM Tris-HCl and MBP-SH2A40 was cleaved into MBP and SH2A40 using TEV-GST. Then, TEV-GST and the MBP protein were removed using GST resin and amylose resin and only pure SH2A40 was obtained (FIG. 5).

Figure 6:
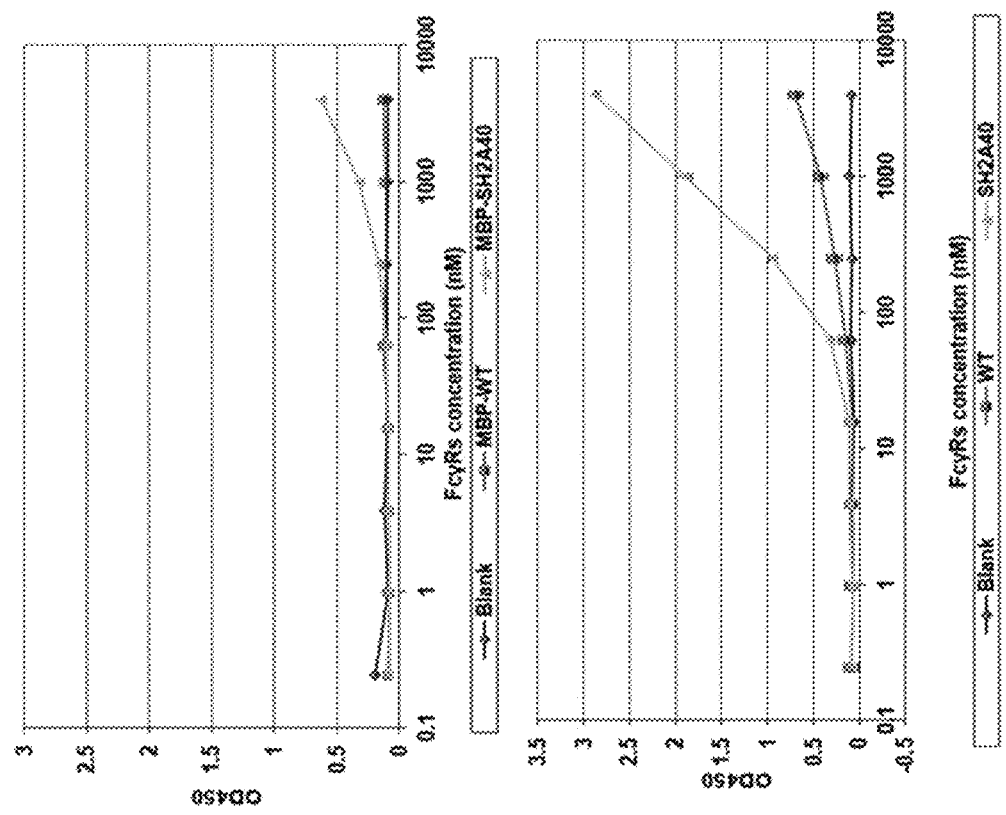
Figure 6:
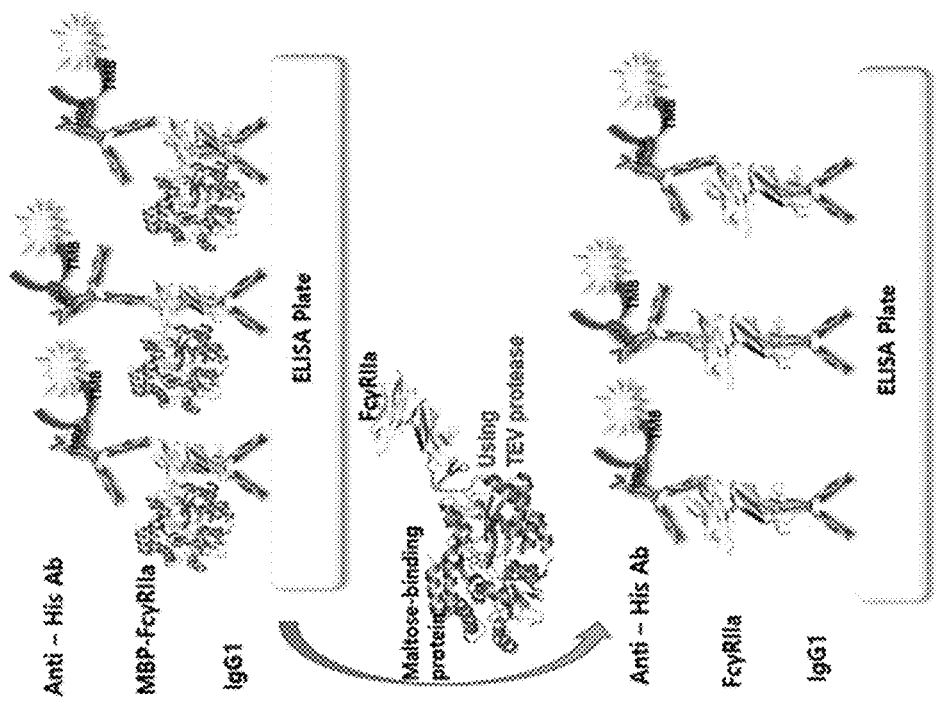

Example 6. Analysis of Binding Ability to IgG1 of FcγRIIa Mutant Expressed in *E. coli* by ELISA ELISA was conducted to investigate the activity of SH2A40. 50 μL of rituximab diluted to 4 μg/mL with 0.05 M $Na_2CO_3$ (pH 9.6) was immobilized onto the Flat Bottom Polystyrene High Bind 96-well microplate (Costar) at 4° C. for 16 hours and blocked with 100 μL of 4% skim milk (GenomicBase) (in 0.05% PBST) at room temperature for 2 hours. After washing with 180 μL of 0.05% PBST for 4 times, 50 μL of WT FcγRIIa and SH2A40 serially diluted with 1% skim milk (in 0.05% PBST) were added to each well and incubated at room temperature for 1 hour. After washing, antibody reaction was conducted at room temperature for 1 hour using 50 μL of anti-His-HRP conjugate (Sigma). After washing, followed by color development by adding 50 μL of 1-Step Ultra TMB-ELISA substrate solution (Thermo Fisher Scientific), the reaction was terminated by adding 50 μL of 2 M $H_2SO_4$ and analysis was conducted using the Epoch microplate spectrophotometer (BioTek) (FIG. 6).

Figure 7:
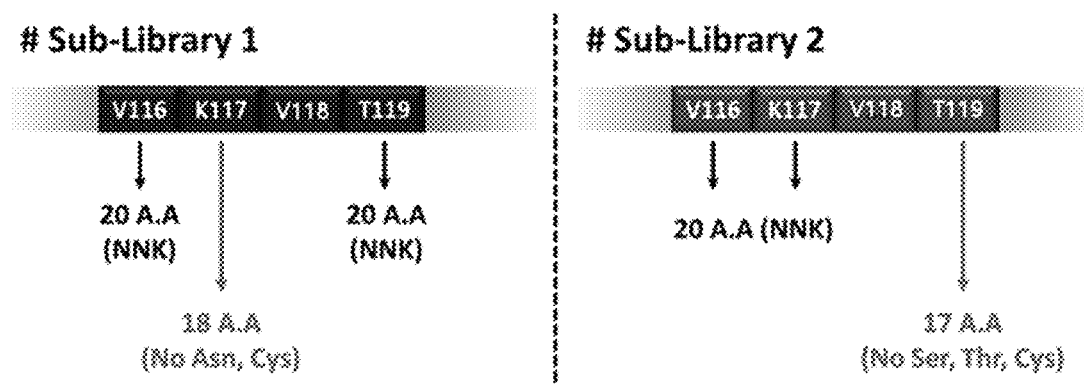

Example 7: Construction of FcγRIIa Mutant Library without Formation of N-Linked Canonical Glycosylation Motif A library was constructed to screen FcγRIIa mutants with high affinity for IgG Fc with no N-linked canonical glycosylation motif (N-X-S/T) formed in the FcγRIIa mutant (SH2A40: K117N, L159Q). The library was constructed while focusing at V116, K117 and T119 positions where N-linked canonical glycosylation motif was formed in SH2A40. The library was constructed using SH2A40 as a template. A reduced codon was used in order to avoid unpaired Cys (FIG. 7).

1. Sub-Library-1: No Asn or Cys Formation at 117th Position pMopac12-NlpA-FcγRIIa(SH2A40)-FLAG was used as a template. NNK degenerate codon was used for the 116th and 119th positions to code 20 amino acids, NNG reduced codon was used for the 117th position to code 13 amino acids, and primers coding individual amino acids were used for the 5 remaining amino acids (Gln, Phe, His, Ile, Tyr). The fragment-1 at the front 116th position of the FcγRIIa gene was amplified using MJ #160 and MJ #112 primers and Vent polymerase (New England Biolab), and the fragment-2 on the rear side was amplified using a mixture of MJ #113-MJ #118 at the same ratio and MJ #161. The prepared two fragments were assembled with Vent polymerase and treated with SfiI (New England Biolab) restriction enzyme.

2. Sub-Library-2: No Ser, Thr or Cys Formation at 119th Position pMopac12-NlpA-FcγRIIa(SH2A40)-FLAG was used as a template. NNK degenerate codon was used for the 116th and 117th positions to code 20 amino acids, NNG reduced codon was used for the 119th position to code 12 amino acids, and primers coding individual amino acids were used for the 5 remaining amino acids (Ala, Gly, Pro, Arg, Trp). The fragment-1 at the front 116th position of the FcγRIIa gene was amplified using MJ #160 and MJ #112 primers and Vent polymerase (New England Biolab), and the fragment-2 on the rear side was amplified using a mixture of MJ #119-MJ #124 at the same ratio and MJ #161. The prepared two fragments were assembled with Vent polymerase and treated with SfiI (New England Biolab) restriction enzyme.

An FcγRIIa library was constructed by transforming the two sub-library genes treated with the restriction enzymes were ligated into Jude1 (theoretical library size: 4.3×10$^4$, experimental library size: 6.3×10$^8$).

Example 8: Isolation of Mutants Such as MG2A28, MG2A45, Etc. Using Established Library by Flow Cytometry (Affinity Analysis for Human Serum IgG)

Figure 8:
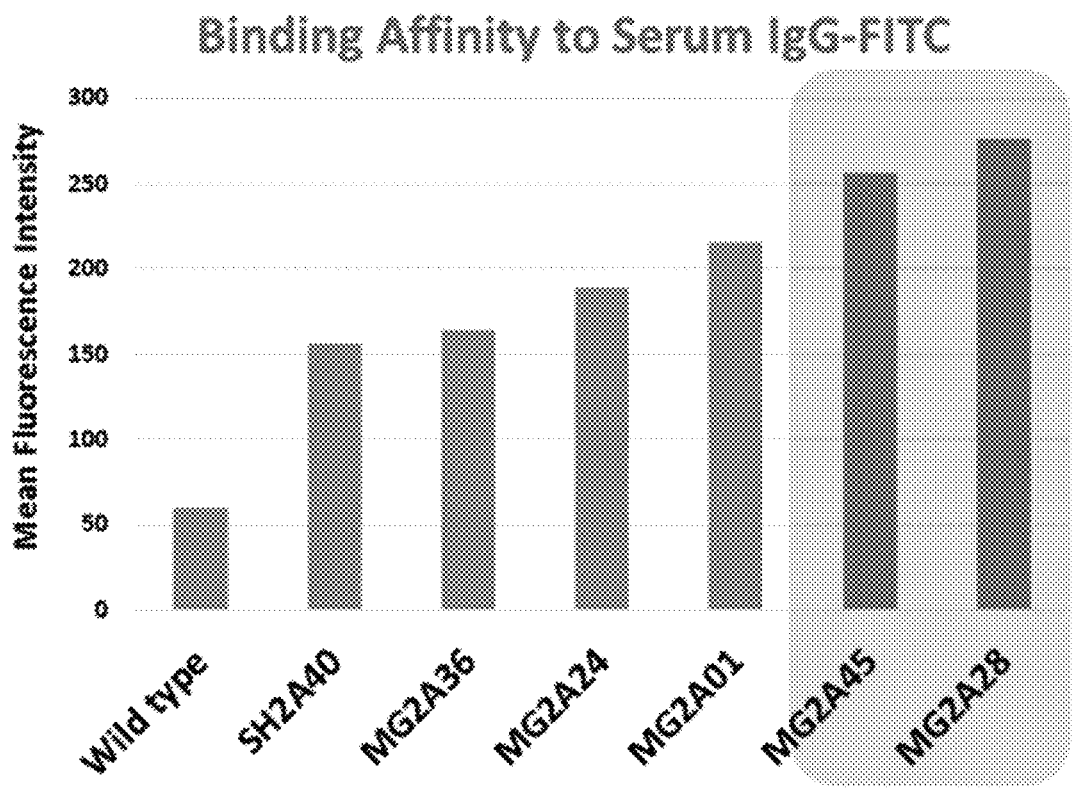

The established library was incubated at 37° C. for 4 hours in 25 mL of TB+2% glucose medium in a 250-mL flask, inoculated to a 500-mL flask containing 100 mL of TB medium at 1:100, and then cultured until OD$_{600}$=0.6. After cooling at 25° C. and 250 rpm for 20 minutes, overexpression was conducted at 25° C. and 250 rpm for 5 hours by adding 1 mM IPTG. After the overexpression, OD$_{600}$ value was measured and a normalized amount of the cells were collected by centrifugation at 14,000 rpm for 1 minute. After resuspending the cells by adding 1 mL of 10 mM Tris-HCl (pH 8.0), centrifugation was conducted for 1 minute. This washing procedure was repeated twice. After resuspending in 1 mL of STE [0.5 M sucrose, 10 mM Tris-HCl, 10 mM EDTA (pH 8.0)], the outer cell membrane was removed by rotating at 37° C. for 30 minutes. After centrifuging and removing the supernatant, resuspension was performed by adding 1 mL of solution A [0.5 M sucrose, 20 mM MgCl$_2$, 10 mM MOPS, pH 6.8]. The resulting solution was centrifuged. After resuspending in 1 mL of a mixture solution prepared by 1 mL of solution A and 20 μL of a 50 mg/mL lysozyme solution, the peptidoglycan layer was removed by rotating at 37° C. for 15 minutes. After centrifuging and removing the supernatant, the remainder was resuspended in 1 mL PBS. 300 μL of the resulting solution was taken, combined with 700 μL of PBS and a human serum IgG-FITC probe (Sigma Aldrich), and then labeled with the fluorescent probe in spheroplasts by rotation at room temperature. After the labeling, followed by washing once with 1 mL of PBS and diluting 20 times in PBS, the top 3% cells exhibiting high fluorescence were recovered by flow cytometry (S3 cell sorter; Bio-Rad). For more effective screening, the sorted cells were sorted again. After amplifying genes by PCR from the resorted cells using MJ #1 and MJ #2 primers and Taq polymerase (Biosesang), a gene-amplified sub-library was constructed by ligation with SfiI restriction enzyme treatment and transformation. After repeating this procedure for a total of 3 rounds, mutants showing higher affinity for the Fc region of human serum IgG were screened by base sequence analysis of more than 50 individual clones (FIG. 8).

Figure 9:
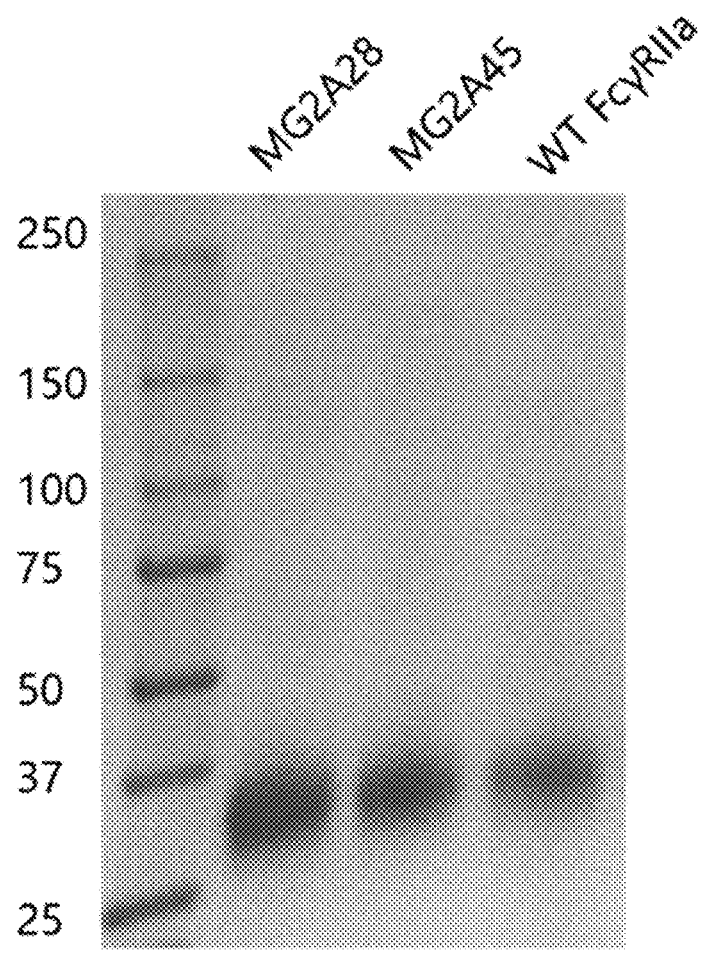

Example 9: Cloning, Expression and Purification of Isolated Mutant for Expression in Mammalian Cells In order to express MG2A28 (SEQ ID NOS 37 and 45) and MG2A45 (SEQ ID NOS 38 and 46) from among the screened mutants in HEK293F cells, pMAZ-FcγRIIa mutant (MG2A28) and pMAZ-FcγRIIa mutant (MG2A45) were prepared by gene amplification by PCR using Vent polymerase and MJ #162 and MJ #163 primers, followed by ligation by treatment with BssHII and XbaI (New England Biolab) restriction enzymes. The genes cloned into the mammalian cell expression vector pMAZ were transfected into HEK293F cells and expressed temporarily at a scale of 300 mL. After culturing was completed, the cells were removed by centrifuging at 2,000 rpm for 10 minutes, and the supernatant was taken and equilibrated using 25×PBS. The resulting solution was filtered through a 0.2-μm bottle top filter (Merck Millipore). After adding 1 mL of a Ni-NTA agarose (Qiagen) slurry equilibrated with PBS, the solution was stirred at 4° C. for 16 hours and then flown into a polypropylene column (Thermo Fisher Scientific). The pass-through solution was taken, bound to a resin and then washed sequentially with 50 mL of 1×PBS, 25 mL of 10 mM imidazole buffer, 25 mL of 20 mM imidazole buffer and 200 μL of 250 mM imidazole buffer. Elution was performed with 2.5 mL of 250 mM imidazole buffer. The collected protein was concentrated with Amicon Ultra-4 (Merck Millipore) and purified by SDS-PAGE (Bio-Rad) (FIG. 9). It was confirmed that the FcγRIIa protein (32 kDa) was purified with high purity on SDS-PAGE.

Figure 10:
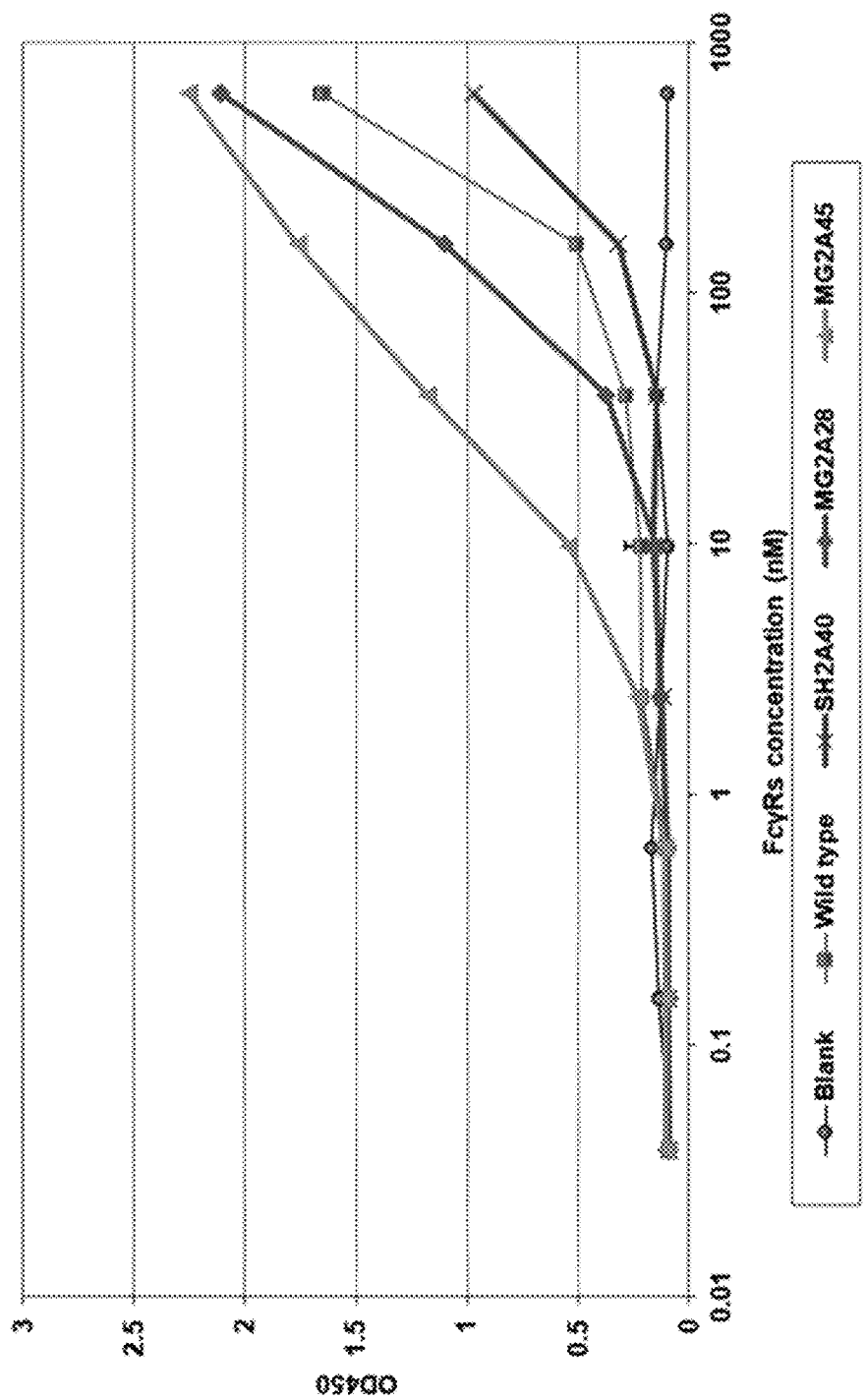

Example 10: ELISA for Analyzing Binding Ability of Mutants for Fc Using Rituximab Consisting of IgG1 Subclass 50 μL of rituximab diluted to 4 μg/mL with 0.05 M Na$_2$CO$_3$ (pH 9.6) was immobilized onto the Flat Bottom Polystyrene High Bind 96-well microplate (Costar) at 4° C. for 16 hours and blocked with 100 μL of 5% BSA (in 0.05% PBST) at room temperature for 2 hours. After washing with 180 μL of 0.05% PBST for 4 times, 50 μL of FcγRIIa mutants serially diluted with a blocking solution were added to each well and incubated at room temperature for 1 hour. After washing, antibody reaction was conducted at room temperature for 1 hour using 50 μL of anti-His-HRP conjugate (Sigma). After washing, followed by color development by adding 50 μL of 1-Step Ultra TMB-ELISA substrate solution (Thermo Fisher Scientific), the reaction was terminated by adding 50 μL of 2 M H$_2$SO$_4$ and analysis was conducted using the Epoch microplate spectrophotometer (BioTek) (FIG. 10). All the experiments were conducted in duplicates. Through ELISA, the binding ability for the Fc region of rituximab and FcγRIIa mutants could be compared and analyzed.

Figure 11:
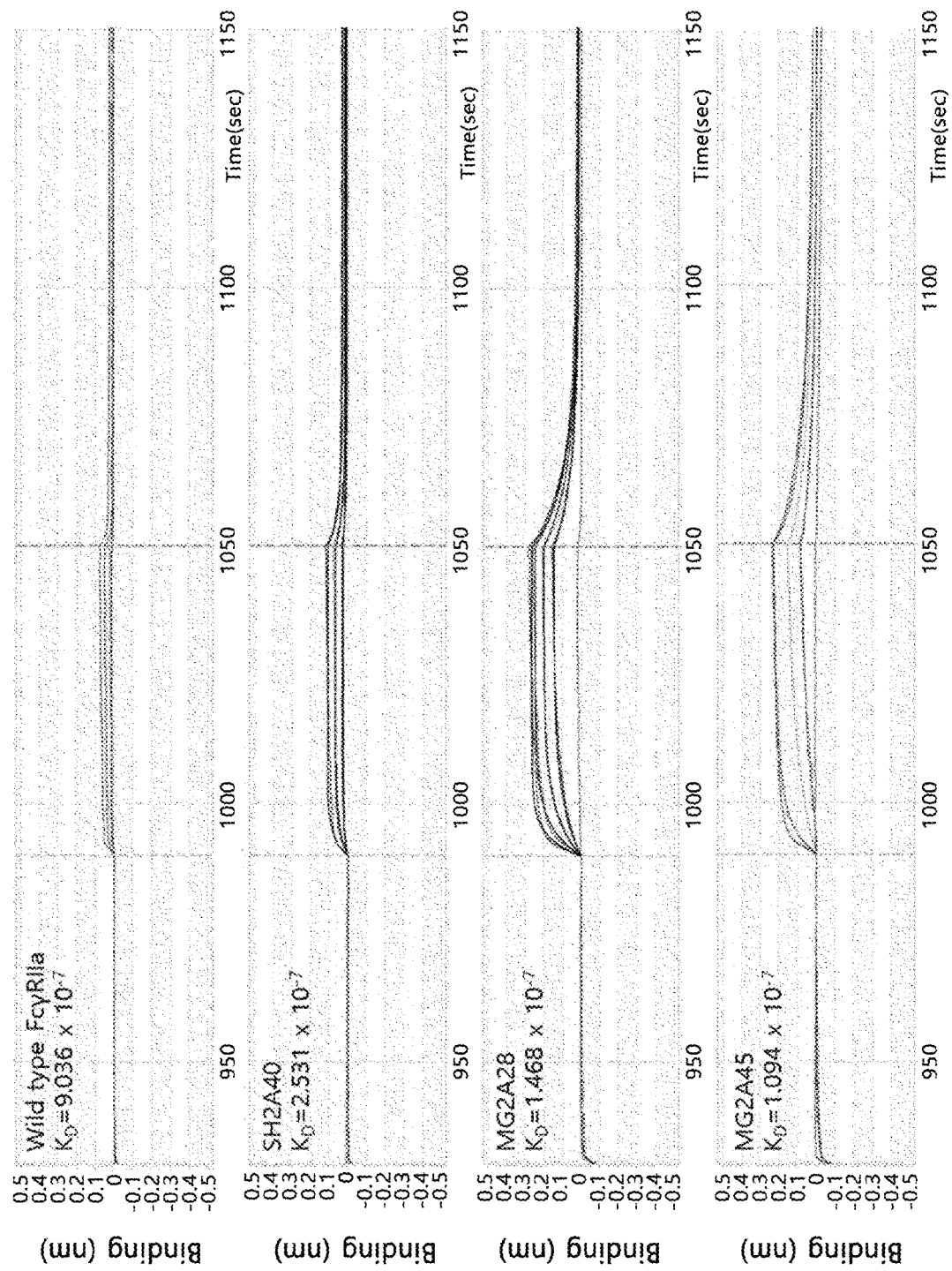

Example 11: Measurement of K$_D$ Value of FcγRIIa Mutant and Rituximab Through Biolayer Interferometry In order to measure the binding ability of IgG1, which is an IgG subclass accounting for about 70% or more of human serum and mainly used in various antibody drugs, to Fc, the affinity of FcγRIIa mutants was measured using rituximab. The binding ability of the FcγRIIa mutants was measured using Blitz (Fortebio). For stable analysis, rituximab antibody was immobilized to an amine-reactive 2nd generation (AR2G) biosensor (Fortebio) diluted with 40 μg/mL of a sodium acetate (pH 5.0) solution, and binding ability was analyzed by reacting with FcγRIIa mutants (wild-type SH2A40, MG2A28, MG2A45) serially diluted with 1× kinetics buffer (Fortebio) (FIG. 11). The Blitz Pro 1.2 software (Fortebio) was used to calculate equilibrium binding constant (K$_D$) (Table 3). As a result, it was confirmed that SH2A40, MG2A28 and MG2A45 screened in the present disclosure have 3.57-fold, 6.16-fold and 8.26-fold increased binding ability for Fc, respectively.

Example 12: Establishment of FcγRIIa Error Prone PCR Library Based on MG2A28 and MG2A45 for Affinity Maturation In order to construct an FcγRIIa mutant library based on MG2A28 and MG2A45, error prone PCR was conducted using pMopac12-NlpA-FcγRIIa (MG2A28, MG2A45)-FLAG as a template. The error prone PCR technique using Taq polymerase (Takara) was employed to introduce random point mutation to the FcγRIIa region. PCR was conducted such that the two mutants MG2A28 and MG2A45 exist at the same ratio of 50%:50% in the library. Point mutation was introduced into 0.3% of nucleotides of the total FcγRIIa genes using MJ #160 and MJ #161 primers. Then, an FcγRIIa library was constructed through treatment with SfiI restriction enzyme, ligation and transformation into Jude1 (library size: $2.6×10^9$, experimental error rate: 0.32%). In the library, the FcγRIIa mutants were displayed on the inner membrane of E. coli.

Example 13: Isolation of Mutants Such as MG2A28.1, MG2A45.1, Etc. Using Established Library and Flow Cytometry (Analysis of Affinity for Human Serum IgG)

Figure 12:
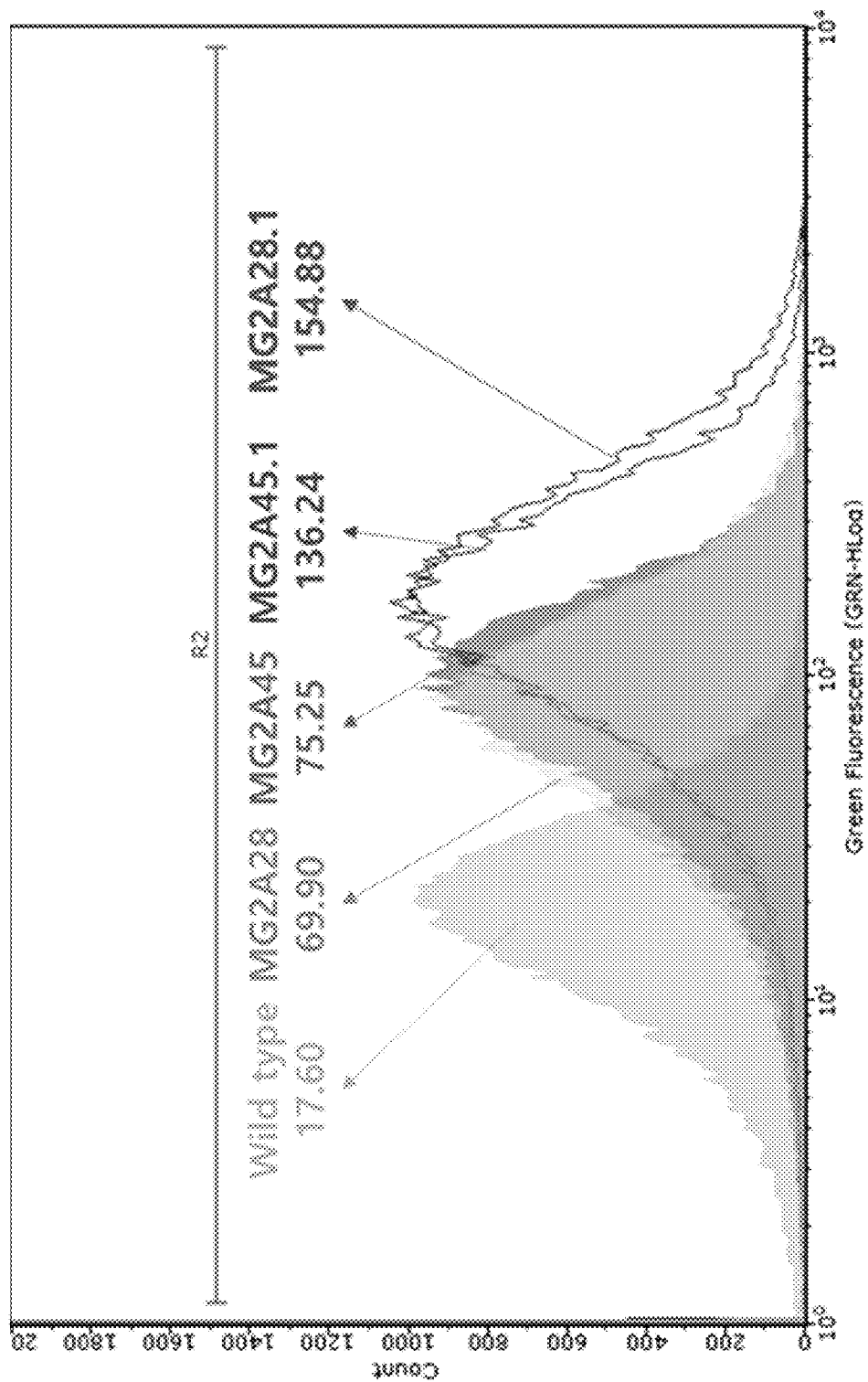

The established library was incubated at 37° C. for 4 hours with a vial (1 mL) of 25 mL of TB+2% glucose medium in a 250-mL flask, and then inoculated in a 500-mL flask containing 100 mL of TB medium at 1:100. After culturing until $OD_{600}$=0.6, followed by cooling at 25° C. and 250 rpm for 20 minutes, overexpression was performed at 25° C. and 250 rpm for 5 hours by adding 1 mM IPTG. After the overexpression, $OD_{600}$ value was measured and a normalized amount of the cells were collected by centrifugation at 14,000 rpm for 1 minute. After resuspending the cells by adding 1 mL of 10 mM Tris-HCl (pH 8.0), centrifugation was conducted for 1 minute. This washing procedure was repeated twice. After resuspending in 1 mL of STE [0.5 M sucrose, 10 mM Tris-HCl, 10 mM EDTA (pH 8.0)], the outer cell membrane was removed by rotating at 37° C. for 30 minutes. After centrifuging and removing the supernatant, resuspension was performed by adding 1 mL of solution A [0.5 M sucrose, 20 mM $MgCl_2$, 10 mM MOPS, pH 6.8]. The resulting solution was centrifuged. After resuspending in 1 mL of a mixture solution prepared by 1 mL of solution A and 20 μL of a 50 mg/mL lysozyme solution, the peptidoglycan layer was removed by rotating at 37° C. for 15 minutes. After centrifuging and removing the supernatant, the remainder was resuspended in 1 mL PBS. 300 μL of the resulting solution was taken, combined with 700 μL of PBS and a human serum IgG-FITC probe (Sigma Aldrich), and then labeled with the fluorescent probe in spheroplasts by rotation at room temperature (1-2 rounds: 20 nM, 3 round: 5 nM). After the labeling, followed by washing once with 1 mL of PBS and diluting 20 times in PBS, the top 3% cells exhibiting high fluorescence were recovered by flow cytometry (S3 cell sorter; Bio-Rad). For more effective screening, the sorted cells were sorted again. After amplifying genes by PCR from the resorted cells using MJ #1 and MJ #2 primers and Taq polymerase (Biosesang), a gene-amplified sub-library was constructed by ligation with SfiI restriction enzyme treatment and transformation. After repeating this procedure for a total of 5 rounds, fluorescence intensity due to binding to IgG-FITC of more than 70 individual clones was analyzed. Through this, the mutants showing high affinity for the Fc region of human serum IgG were screened. It was confirmed through base sequencing that an MG2A28-based mutant and an MG2A45-based mutant were isolated (FIG. 12).

Figure 13:
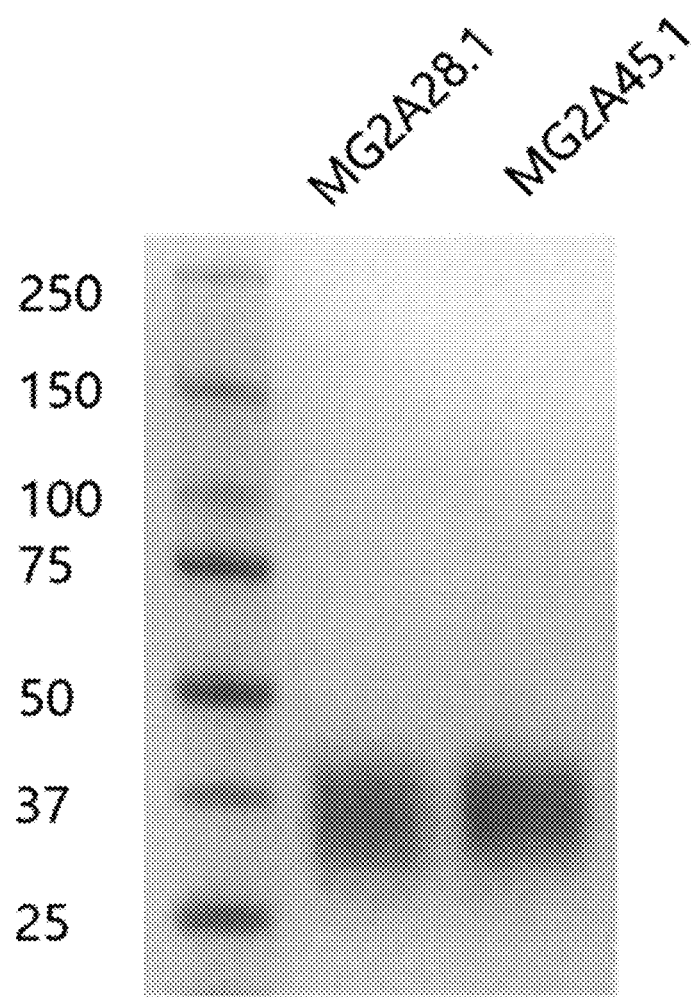

Example 14: Cloning for Expression of Isolated Mutants, Expression and Purification in Mammalian Cells In order to express MG2A28.1 (SEQ ID NOS 39 and 47) and MG2A45.1 (SEQ ID NOS 40 and 48) from among the screened mutants in HEK293F cells, pMAZ-FcγRIIa mutant (MG2A28.1) and pMAZ-FcγRIIa mutant (MG2A45.1) were prepared by gene amplification by PCR using Vent polymerase and MJ #162 and MJ #163 primers, followed by ligation by treatment with BssHII and XbaI (New England Biolab) restriction enzymes. The genes cloned into the mammalian cell expression vector pMAZ were transfected into HEK293F cells and expressed temporarily at a scale of 300 mL. After culturing was completed, the cells were removed by centrifuging at 2,000 rpm for 10 minutes, and the supernatant was taken and equilibrated using 25×PBS. The resulting solution was filtered through a 0.2-μm bottle top filter (Merck Millipore). After adding 1 mL of a Ni-NTA agarose (Qiagen) slurry equilibrated with PBS, the solution was stirred at 4° C. for 16 hours and then flown into a polypropylene column (Thermo Fisher Scientific). The pass-through solution was taken, bound to a resin and then washed sequentially with 50 mL of 1×PBS, 25 mL of 10 mM imidazole buffer, 25 mL of 20 mM imidazole buffer and 200 μL of 250 mM imidazole buffer. Elution was performed with 2.5 mL of 250 mM imidazole buffer. The collected protein was concentrated with Amicon Ultra-4 (Merck Millipore) and purified by SDS-PAGE (Bio-Rad) (FIG. 13). It was confirmed that the FcγRIIa protein (32 kDa) was purified with high purity on SDS-PAGE.

Figure 14:
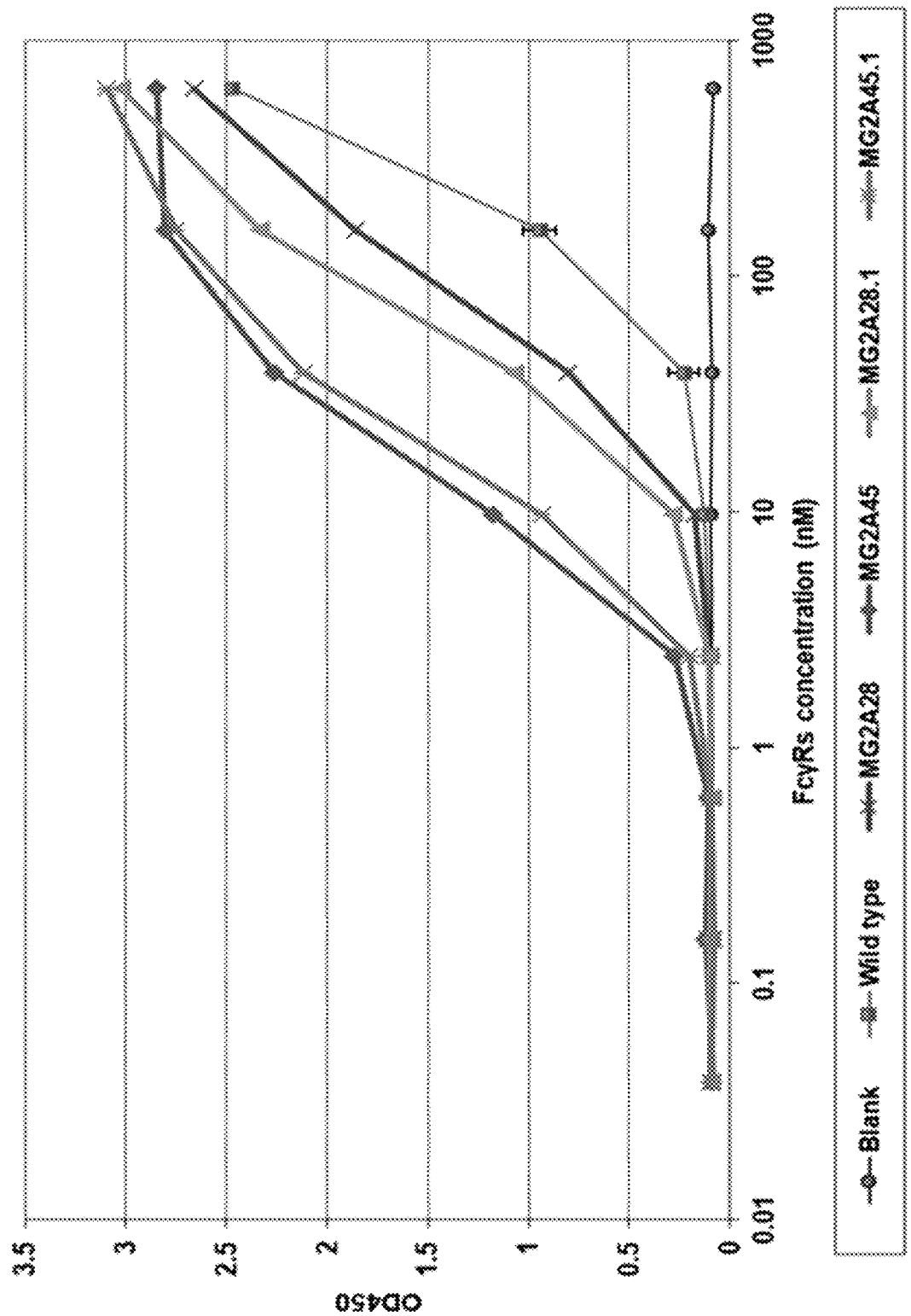

Example 15: ELISA for Analyzing Binding Ability of Mutants for Fc Using Rituximab Consisting of IgG1 Subclass 50 μL of rituximab diluted to 4 μg/mL with 0.05 M $Na_2CO_3$ (pH 9.6) was immobilized onto the Flat Bottom Polystyrene High Bind 96-well microplate (Costar) at 4° C. for 16 hours and blocked with 100 μL of 5% BSA (in 0.05% PBST) at room temperature for 2 hours. After washing with 180 μL of 0.05% PBST for 4 times, 50 μL of FcγRIIa mutants serially diluted with a blocking solution were added to each well and incubated at room temperature for 1 hour. After washing, antibody reaction was conducted at room temperature for 1 hour using 50 μL of anti-His-HRP conjugate (Sigma). After washing, followed by color development by adding 50 μL of 1-Step Ultra TMB-ELISA substrate solution (Thermo Fisher Scientific), the reaction was terminated by adding 50 μL of 2 M $H_2SO_4$ and analysis was conducted using the Epoch microplate spectrophotometer (BioTek) (FIG. 14). All the experiments were conducted in duplicates. Through ELISA, the binding ability for the Fc region of rituximab and FcγRIIa mutants (wild type, MG2A28, MG2A45, MG2A28.1, MG2A45.1) could be compared and analyzed.

Figure 15:
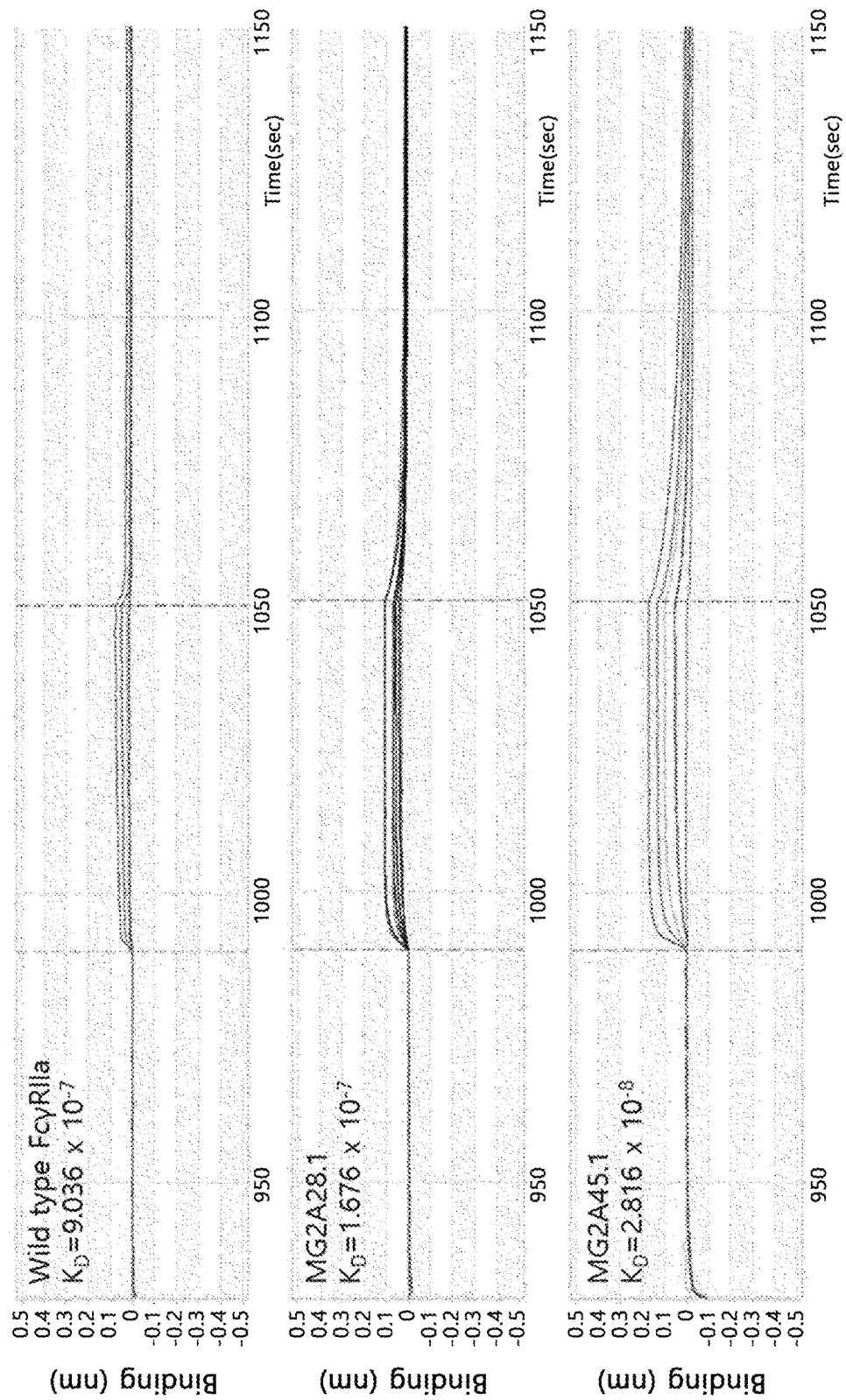

Example 16: Measurement of $K_D$ Value of FcγRIIa Mutant and Rituximab Through Biolayer Interferometry In order to measure the binding ability of IgG1, which is an IgG subclass accounting for about 70% or more of human serum and mainly used in various antibody drugs, to Fc, the affinity of FcγRIIa mutants was measured using rituximab. The binding ability of the FcγRIIa mutants was measured using Blitz (Fortebio). For stable analysis, rituximab antibody was immobilized to an amine-reactive 2nd generation (AR2G) biosensor (Fortebio) diluted with 40 μg/mL of a sodium acetate (pH 5.0) solution, and binding ability was analyzed by reacting with FcγRIIa mutants (MG2A28.1, MG2A45.1) serially diluted with 1× kinetics buffer (Fortebio) (FIG. 15). The Blitz Pro 1.2 software (Fortebio) was used to calculate equilibrium binding constant ($K_D$) (Table 4). As a result, it was confirmed that MG2A28.1 and MG2A45.1 screened in the present disclosure have 5.39-fold and 32.09-fold increased binding ability for Fc, respectively.

Figure 16:
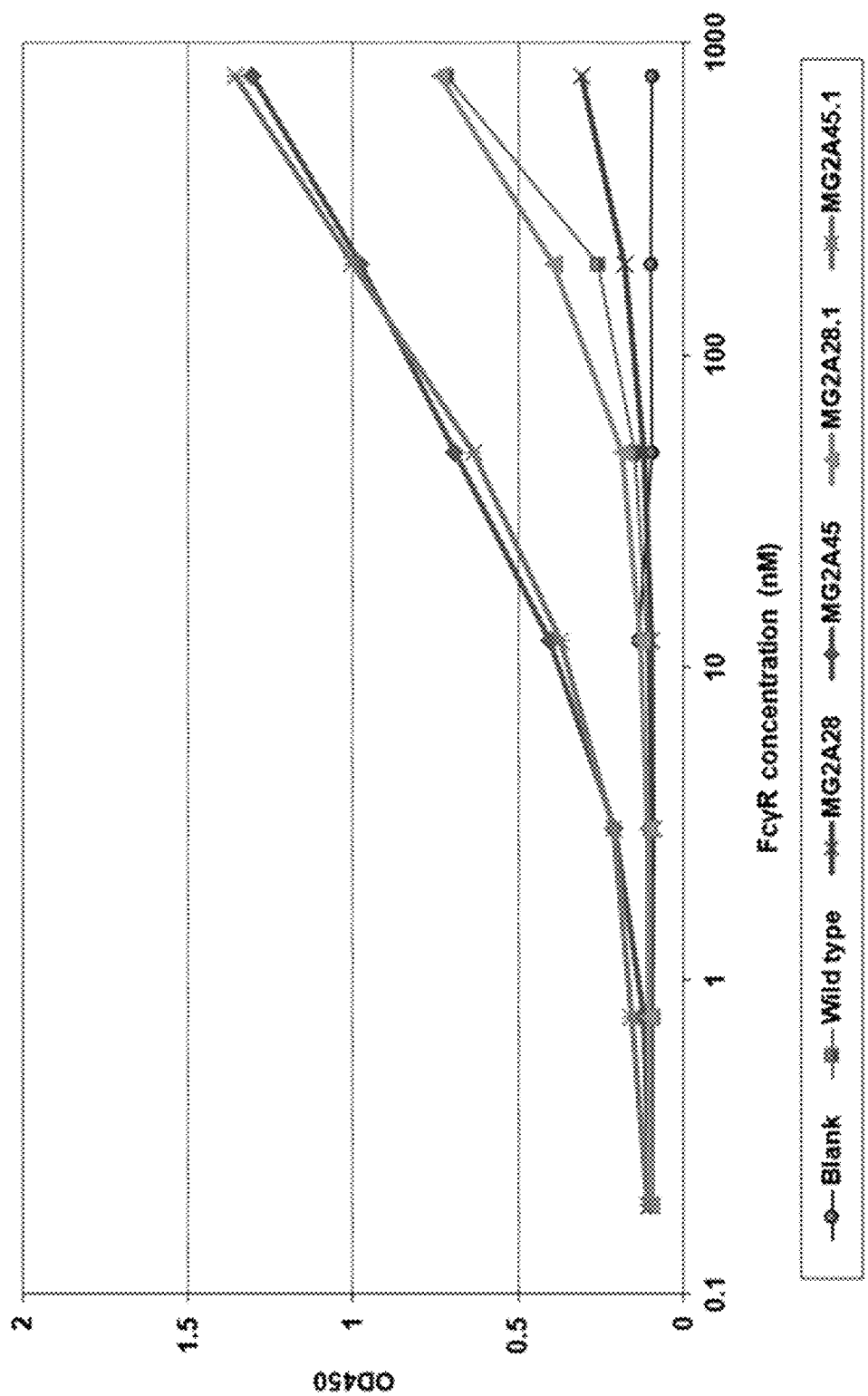

Example 17: Analysis of Binding Ability to Mouse Serum IgG by ELISA for Mammalian Experiment Using Mouse Model 50 μL of mouse serum IgG diluted to 4 μg/mL with 0.05 M $Na_2CO_3$ (pH 9.6) was immobilized onto the Flat Bottom Polystyrene High Bind 96-well microplate (Costar) at 4° C. for 16 hours and blocked with 100 μL of 5% BSA (in 0.05% PBST) at room temperature for 2 hours. After washing with 180 μL of 0.05% PBST for 4 times, 50 μL of FcγRIIa mutants (wild type, MG2A28, MG2A45, MG2A28.1, MG2A45.1) serially diluted with a blocking solution were added to each well and incubated at room temperature for 1 hour. After washing, antibody reaction was conducted at room temperature for 1 hour using 50 μL of anti-His-HRP conjugate (Sigma). After washing, followed by color development by adding 50 μL of 1-Step Ultra TMB-ELISA substrate solution (Thermo Fisher Scientific), the reaction was terminated by adding 50 μL of 2 M $H_2SO_4$ and analysis was conducted using the Epoch microplate spectrophotometer (BioTek) (FIG. 16). All the experiments were conducted in duplicates. Through ELISA, the binding ability for the mouse serum IgG and FcγRIIa mutants (wild type, MG2A28, MG2A45, MG2A28.1, MG2A45.1) could be compared and analyzed. All the mutants excluding MG2A28 showed similar or higher affinity to mouse serum IgG when compared with the wild type. Especially, the MG2A45 and MG2A45.1 mutants showed the highest affinity for the mouse serum IgG.

Example 18: Introduction of Point Mutation for Investigation of Affinity for Fc of FcγRIIb Having about 96% Homology to FcγRIIa Experiment was conducted to analyze the effect of the screened point mutants on FcγRIIb (SEQ ID NOS 41 and 49). For this, the pMopac12-NlpA-FcγRIIb-FLAG plasmid was used as a template, and the Quikchange site directed mutagenesis (Agilent) technique was employed to introduce R55H and L159Q from among the MG2A45.1 point mutations (R55H, K117N, T119V, L159Q, V171E) to the FcγRIIb gene. MJ #200, MJ #201, MJ #202 and MJ #203 primers were used for introduction of each point mutation. After conducting PCR using Pfu turbo polymerase (Agilent), incubation was performed at 37° C. for 3 hours for DpnI (New England Biolab) restriction enzyme treatment. After transformation of the prepared gene, it was confirmed through base sequencing that the point mutation was introduced successfully. The assembly PCR technique was used for introduction of the three point mutations K117N, T119V and V171E. A plasmid with R55H and L159Q introduced by Quikchange site directed mutagenesis was used as a template. Two fragments were amplified using MJ #160, MJ #197, MJ #198 and MJ #199 primers and vent polymerase (New England Biolab), and MJ #160 and MJ #199 were assembled. Then, through SfiI restriction enzyme treatment, ligation, transformation and base sequencing, the preparation of the pMopac12-NlpA-FcγRIIb(MG2B45.1)-FLAG gene in which all the five point mutations of MG2A45.1 was inserted was completed.

Figure 17:
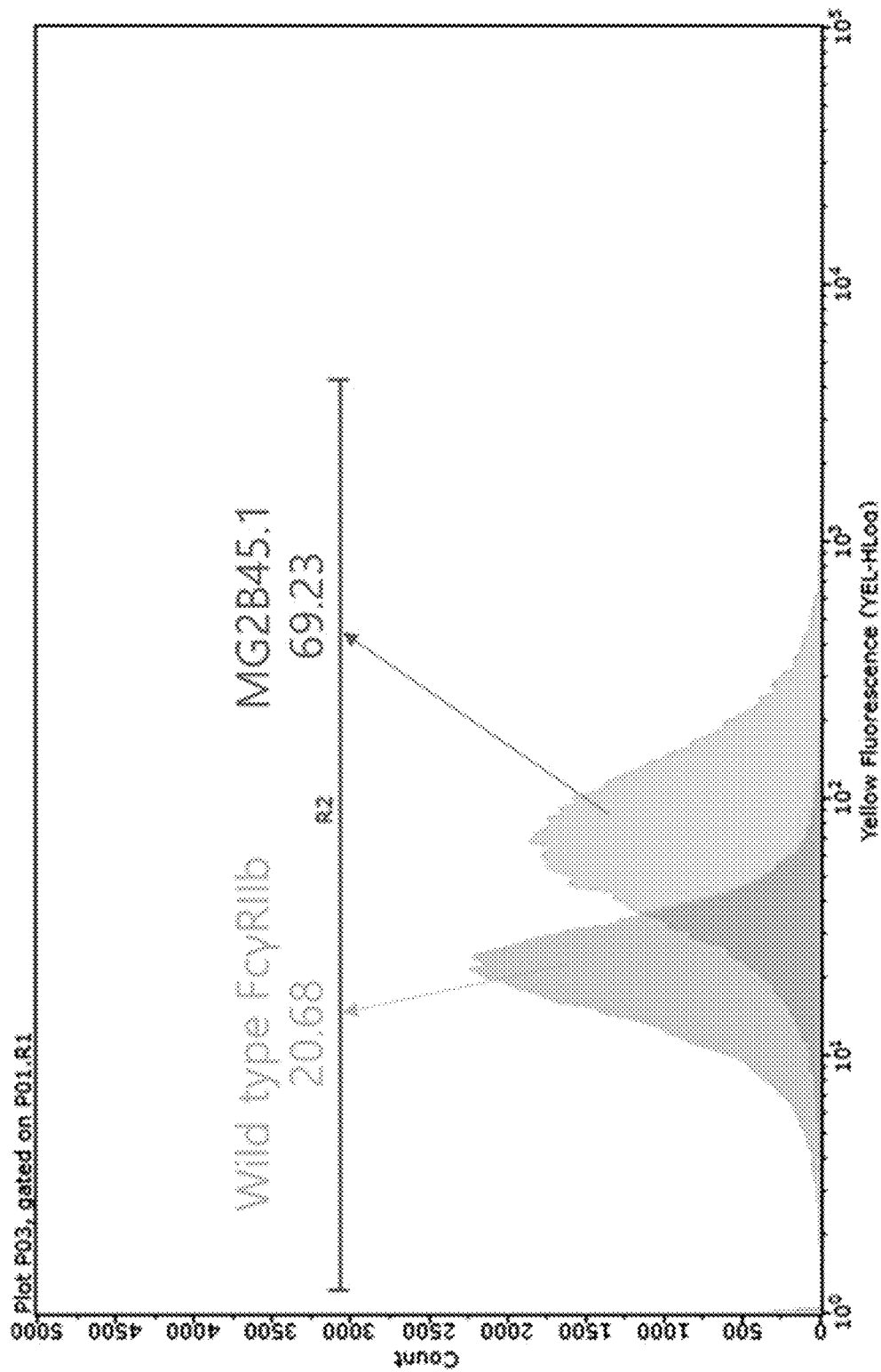

Example 19: Comparison of Affinity of Wild-Type FcγRIIb and MG2A45.1 Mutation-Introduced FcγRIIb (MG2B45.1) for Human Serum IgG-FITC The affinity of the FcγRIIb mutant (MG2B45.1) (SEQ ID NOS 42 and 50) for human serum IgG-FITC was compared with that of the wild-type FcγRIIb. An inoculum precultured in 5 mL of TB+2% glucose medium was inoculated to 5 mL of TB medium at 1:100 until $OD_{600}$=0.6. After cooling at 25° C. and 250 rpm for 20 minutes, overexpression was performed at 25° C. and 250 rpm for 5 hours by adding 1 mM IPTG. After the overexpression, $OD_{600}$ value was measured and a normalized amount of the cells were collected by centrifugation at 14,000 rpm for 1 minute. After resuspending the cells by adding 1 mL of 10 mM Tris-HCl (pH 8.0), centrifugation was conducted for 1 minute. This washing procedure was repeated twice. After resuspending in 1 mL of STE [0.5 M sucrose, 10 mM Tris-HCl, 10 mM EDTA (pH 8.0)], the outer cell membrane was removed by rotating at 37° C. for 30 minutes. After centrifuging and removing the supernatant, resuspension was performed by adding 1 mL of solution A [0.5 M sucrose, 20 mM $MgCl_2$, 10 mM MOPS, pH 6.8]. The resulting solution was centrifuged. After resuspending in 1 mL of a mixture solution prepared by 1 mL of solution A and 20 μL of a 50 mg/mL lysozyme solution, the peptidoglycan layer was removed by rotating at 37° C. for 15 minutes. After centrifuging and removing the supernatant, the remainder was resuspended in 1 mL PBS. 300 μL of the resulting solution was taken, combined with 700 μL of PBS and a human serum IgG-FITC probe (Sigma Aldrich), and then labeled with the fluorescent probe in spheroplasts by rotation at room temperature (1-2 rounds: 20 nM, 3 round: 5 nM). After the labeling, followed by washing once with 1 mL of PBS and diluting 20 times in PBS, the fluorescence signal from the human IgG-FITC bound to FcγRIIb was analyzed using Guava (Merck Millipore) (FIG. 17).

Example 20: Cloning of Bevacizumab scFv and Bevacizumab scFv-FcγRIIa Mutant for Investigation of Increase in Serum Half-Life The VH gene was amplified using the heavy chain of bevacizumab as a template and using Vent polymerase and BR #1 and BR #2 primers, and the VL gene was amplified using the light chain bevacizumab as a template and using BR #4 and BR #5 primers. The amplified genes were assembled using a GS linker introduced into a BR #3 primer, and bevacizumab scFv was prepared through treatment with BssHII and XbaI (New England Biolab) restriction enzymes, ligation and cloning into the pMAZ vector, which is a vector for expression in mammalian cells. The wild-type FcγRIIa and FcγRIIa mutant were amplified using BR #6 and BR #7 primers, respectively. The amplified FcγRIIa genes was assembled using a GS linker introduced into BR #6 to obtain bevacizumab scFv-FcγRIIa wild type and bevacizumab scFv-MG2A45.1 genes. pMAZ-bevacizumab scFv, pMAZ-bevacizumab scFv-FcγRIIa wild type and pMAZ-bevacizumab scFv-MG2A45.1 were prepared by treating the amplified genes with BssHII and XbaI (New England Biolab) restriction enzymes, ligating and cloning into the pMAZ vector, which is a vector for expression in mammalian cells. The primers used in this example are described in Table 2.

TABLE 2

| Primer # | Sequence (5'→3') |
|---|---|
| BR#1 (SEQ ID NO 51) | CGCAGCGAGCGCGCACTCCGAGGTGCAGCTGGTGGAGAGC |
| BR#2 (SEQ ID NO 52) | ACTAGAGACAGTCACCAGTGTACCCT |
| BR#3 (SEQ ID NO 53) | AGGGTACACTGGTGACTGTCTCTAGTGGTGGAGGCGGATCAGGCGGTGGCGGCAGTGGAGGGGGTGGTAGCGGCGGAGGAGGTTCCGACATCCAGATGACTCAATCACCCAGT |
| BR#4 (SEQ ID NO 54) | CCCTAAAATCTAGATCACTAGTGATGGTGATGATGATGTGATCCGCCGGTCCGCTTAATCTCCACTTTGGTTC |
| BR#5 (SEQ ID NO 55) | GGTCCGCTTAATCTCCACTTTGGTTC |
| BR#6 (SEQ ID NO 56) | GAACCAAAGTGGAGATTAAGCGGACCGGCGGAGGCGGGAGTCAGGCTGCCCCACCGAAAG |
| BR#7 (SEQ ID NO 57) | TTTTAGGGTCTAGATCACTAGTGATGGTGATGATGATGTGATCCGCCAATCACGCCCATCGGTGAGCTG |

Figure 18:
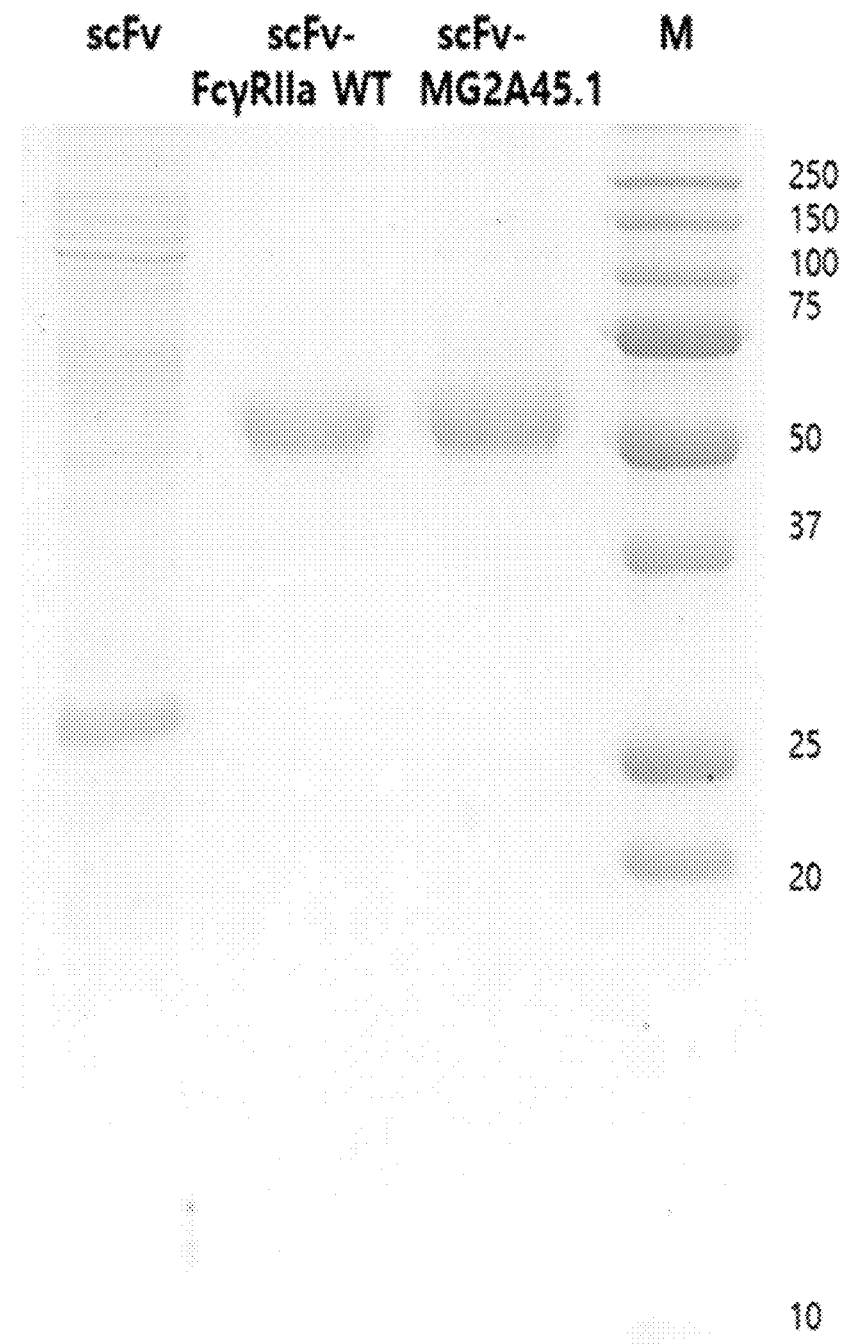

Example 21: Expression and Purification of Bevacizumab scFv and Bevacizumab scFv-FcγRIIa Mutant The prepared genes were expressed in Expi 293F cells temporarily at a scale of 300 mL. After culturing was completed, the cells were removed by centrifuging at 7500 rpm for 15 minutes, and the supernatant was taken and equilibrated using 25×PBS. The resulting solution was filtered through a 0.2-μm bottle top filter (Merck Millipore). After adding 1 mL of a Ni-NTA agarose (Qiagen) slurry equilibrated with PBS, the solution was stirred at 4° C. for 16 hours and then flown into a polypropylene column (Thermo Fisher Scientific). Then, the solution washed sequentially with 25 mL of 10 mM imidazole buffer, 25 mL of 20 mM imidazole buffer and 250 μL of 250 mM imidazole buffer. Elution was performed with 4 mL of 250 mM imidazole buffer. The collected protein was concentrated with Amicon Ultra-4 (Merck Millipore) and purified by SDS-PAGE (Bio-Rad) (FIG. 18).

Figure 19:
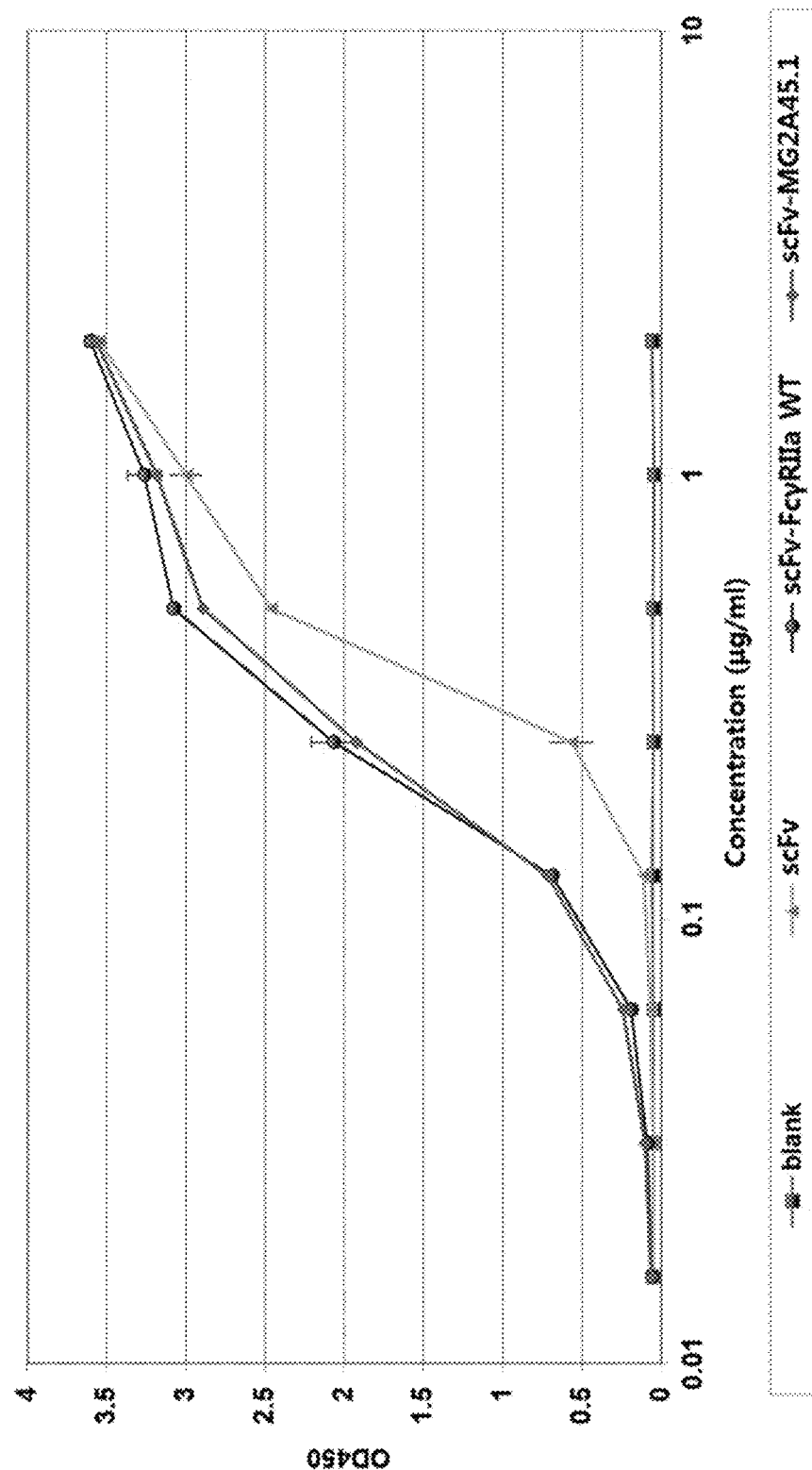

Example 22: ELISA Using VEGF for Analysis of Activity and Binding Ability of Bevacizumab scFv and Bevacizumab scFv-FcγRIIa Mutant Produced Through Mammalian Cell Culturing 50 μL of VEGF (Genscript) diluted to 500 ng/mL with 0.05 M $Na_2CO_3$ (pH 9.6) was immobilized onto the Flat Bottom Polystyrene High Bind 96-well microplate (Costar) at 4° C. for 16 hours and blocked with 100 μL of 5% BSA (in 0.05% PBST) at room temperature for 1 hour. After washing with 180 μL of 0.05% PBST for 4 times, 50 μL of bevacizumab scFv, bevacizumab scFv-FcγRIIa-wild type and bevacizumab scFv-MG2A45.1 proteins serially diluted with a blocking solution were added to each well and incubated at room temperature for 1 hour. After washing, 50 μL of 20 μg/mL human serum IgG was added to each well in order to prevent crosslinking between the Fc domain of the secondary antibody anti-His antibody-HRP conjugate (Sigma-Aldrich) and FcγRIIa, and reaction was conducted at room temperature for 1 hour. After washing, antibody reaction was conducted at room temperature for 1 hour using 50 μL of anti-His-HRP conjugate. After washing, followed by color development by adding 50 μL of 1-Step Ultra TMB-ELISA substrate solution (Thermo Fisher Scientific), the reaction was terminated by adding 50 μL of 2 M $H_2SO_4$ and absorbance was analyzed at 450 nm using the Epoch microplate spectrophotometer (BioTek). All the experiments were conducted in duplicates. Through ELISA, the binding activity of the bevacizumab scFv fused with the γRIIa mutants for the VEGF could analyzed. As a result, it was confirmed that the FcγRIIa wild type and the FcγRIIa mutant MG2A45.1 retain the characteristic VEGF binding ability of bevacizumab scFv after fusion with bevacizumab scFv (FIG. 19). In addition, it was confirmed that the FcγRIIa-fused protein showed higher binding ability on ELISA because FcγRIIa has a tendency to form a dimer via noncovalent bonding (Maxwell, K. F., M. S. Powell, M. D. Hulett, P. A. Barton, I. F. McKenzie, T. P. Garrett, and P. M. Hogarth. 1999. Crystal structure of the human leukocyte Fc receptor, FcγRIIa. Nat. Struct. Biol. 6: 437-442).

Figure 20:
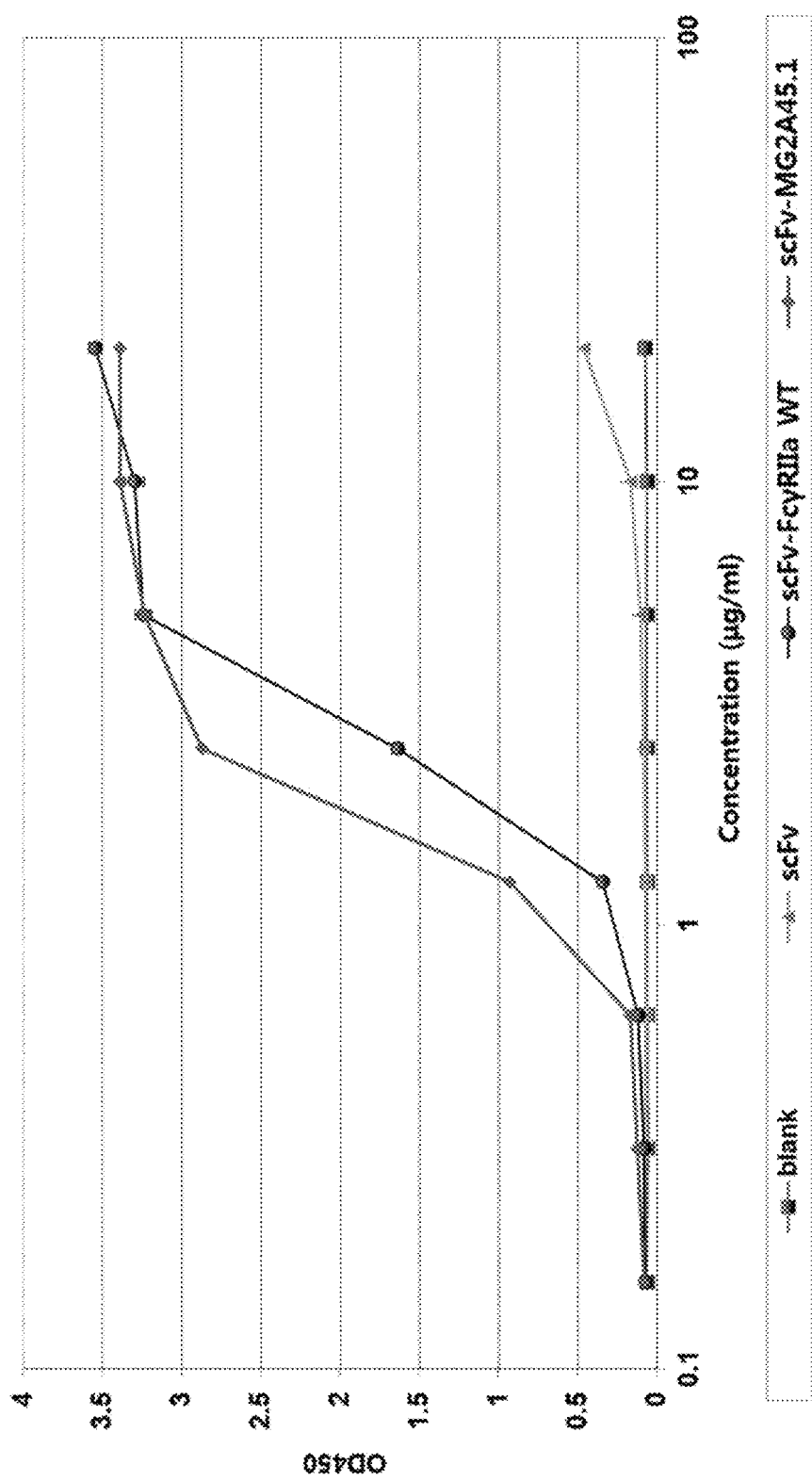

Example 23: ELISA Using Rituximab for Analysis of Activity and Binding Ability of Bevacizumab scFv and Bevacizumab scFv-FcγRIIa Mutant Produced Through Mammalian Cell Culturing 50 μL of rituximab diluted to 4 μg/mL with 0.05 M $Na_2CO_3$ (pH 9.6) was immobilized onto the Flat Bottom Polystyrene High Bind 96-well microplate (Costar) at 4° C. for 16 hours and blocked with 100 μL of 5% BSA (in 0.05% PBST) at room temperature for 1 hour. After washing with 180 μL of 0.05% PBST for 4 times, 50 μL of bevacizumab scFv, bevacizumab scFv-FcγRIIa-wild type and bevacizumab scFv-MG2A45.1 proteins serially diluted with a blocking solution were added to each well and incubated at room temperature for 1 hour. After washing, antibody reaction was conducted at room temperature for 1 hour using 50 μL of anti-His-HRP conjugate (Sigma-Aldrich). After washing, followed by color development by adding 50 μL of 1-Step Ultra TMB-ELISA substrate solution (Thermo Fisher Scientific), the reaction was terminated by adding 50 μL of 2 M $H_2SO_4$ and absorbance was analyzed using the Epoch microplate spectrophotometer (BioTek). All the experiments were conducted in duplicates. Through ELISA, it was confirmed that bevacizumab scFv-FcγRIIa wild type and bevacizumab scFv-FcγRIIa-MG2A45.1 excluding bevacizumab scFv without FcγRIIa retain binding ability to rituximab consisting of IgG1 Fc. In addition, it was confirmed that the MG2A45.1 fusion protein with improved binding ability to Fc shows increased binding ability to rituximab, which reveals that the characteristics of wild type FcγRIIa and its mutant MG2A45.1 are retained after fusion with bevacizumab scFv (FIG. 20).

While the exemplary embodiments have been shown and described, it will be understood by those skilled in the art that various changes in form and details may be made thereto without departing from the spirit and scope of this disclosure as defined by the appended claims. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A polypeptide comprising an Fc-gamma receptor mutant, wherein the mutant is an Fc-gamma receptor mutant containing a sequence wherein the 117th amino acid from SEQ ID NO 43 or SEQ ID NO 49 is substituted with asparagine (N) and the 159th amino acid is substituted with glutamine (Q).

2. The polypeptide according to claim 1, wherein the mutant is an Fc-gamma receptor mutant further comprising one or more amino acid substitution selected from a group consisting of the 55th amino acid, the 86th amino acid, the 119th amino acid, the 127th amino acid and the 171st amino acid.

3. The polypeptide according to claim 2, wherein the mutant is an Fc-gamma receptor mutant comprising one or more amino acid substitution selected from a group consisting of substitution of the 55th amino acid with histidine (H), substitution of the 86th amino acid with aspartic acid (D), substitution of the 119th amino acid with methionine (M) or valine (V), substitution of the 127th amino acid with leucine (L) and substitution of the 171st amino acid with glutamic acid (E).

4. The polypeptide according to claim 1, wherein the mutant comprising the amino acid substitution has improved binding ability to an Fc region of an IgG antibody when compared with the wild-type Fc-gamma receptor.

5. A nucleic acid molecule encoding the polypeptide according to claim 1.

6. A vector comprising the nucleic acid molecule according to claim 5.

7. A host cell comprising the vector according to claim 6.

8. A composition comprising the polypeptide according to claim 1, a nucleic acid molecule encoding said polypeptide or a vector comprising said nucleic acid molecule.

9. The composition according to claim 8, wherein the composition is for detecting an IgG antibody or an Fc region of the IgG antibody comprised in a sample.

10. A kit for detecting an IgG antibody or an Fc region of the IgG antibody, which comprises the composition according to claim 9.

11. A fusion protein or fusion peptide wherein the polypeptide according to claim 1 is bound to a physiologically active protein or a physiologically active peptide, wherein the fusion protein or fusion peptide has increased in vivo half-life due to increased retention in vivo.

12. A method for preparing a polypeptide comprising an Fc-gamma receptor mutant, which comprises:
   a) a step of culturing a host cell comprising a vector comprising a nucleic acid molecule encoding the polypeptide according to claim 1; and
   b) a step of recovering a polypeptide expressed by the host cell.

13. A method for purifying an IgG antibody or an Fc region of the IgG antibody comprised in a sample, which comprises:
   a) a step of binding the polypeptide according to claim 1 to a sample comprising an IgG antibody or an Fc region of the IgG antibody by mixing them together; and
   b) a step of purifying the IgG antibody or the Fc region of the IgG antibody with the polypeptide bound.

* * * * *